US009826921B2

(12) United States Patent
Griffiths et al.

(10) Patent No.: US 9,826,921 B2
(45) Date of Patent: Nov. 28, 2017

(54) DETECTION OF HYPOKINETIC AND HYPERKINETIC STATES

(75) Inventors: Robert Irwin Griffiths, Beaconsfield Upper (AU); Malcolm Kenneth Horne, Malvern East (AU)

(73) Assignee: Global Kinetics Corporation Limited, Melbourne (AU)

( * ) Notice: Subject to any disclaimer, the term of this patent is extended or adjusted under 35 U.S.C. 154(b) by 1213 days.

(21) Appl. No.: 12/997,540

(22) PCT Filed: Jun. 12, 2009

(86) PCT No.: PCT/SU2009/000751
§ 371 (c)(1),
(2), (4) Date: Dec. 10, 2010

(87) PCT Pub. No.: WO2009/149520
PCT Pub. Date: Dec. 17, 2009

(65) Prior Publication Data
US 2011/0098608 A1    Apr. 28, 2011

(30) Foreign Application Priority Data

Jun. 12, 2008  (AU) ................................ 2008902982
Jun. 9, 2009   (AU) ................................ 2009902616

(51) Int. Cl.
*A61B 5/103*     (2006.01)
*A61B 5/11*      (2006.01)
*A61B 5/00*      (2006.01)

(52) U.S. Cl.
CPC ........... *A61B 5/1114* (2013.01); *A61B 5/1123* (2013.01); *A61B 5/4082* (2013.01);
(Continued)

(58) Field of Classification Search
CPC ...... A61B 5/4528; A61B 5/1071; A61B 5/103
(Continued)

(56) References Cited

U.S. PATENT DOCUMENTS 4,306,291 A   12/1981  Zilm et al.
4,730,253 A    3/1988  Gordon
(Continued)

FOREIGN PATENT DOCUMENTS

EP    0535508    4/1993
EP    1595497    11/2005
(Continued)

OTHER PUBLICATIONS

Tremorwatch, Printed from http://www.salusa.se/Filer/Produktinfo/Aktivitet/tremorwatch.pdf, printed Aug. 4, 2011, 2 pgs.
(Continued)

*Primary Examiner* — Daniel Cerioni
(74) *Attorney, Agent, or Firm* — Banner & Witcoff, Ltd.

(57) ABSTRACT

The present invention relates to an automated method of determining a kinetic state of a person. The method obtains accelerometer data from an accelerometer worn on an extremity of the person and processes the accelerometer data to determine a measure for the kinetic state. The present invention further relates to a device for determining a kinetic state of a person. The device comprises a processor configured to process data obtained from an accelerometer worn on an extremity of the person and to determine from the data a measure for the kinetic state. In the method and system the kinetic state is at least one of bradykinesia, dyskinesia, and hyperkinesia.

17 Claims, 11 Drawing Sheets

(52) U.S. Cl.
CPC ........... *A61B 5/7214* (2013.01); *A61B 5/1104* (2013.01); *A61B 5/6824* (2013.01); *A61B 5/7203* (2013.01); *A61B 2562/0219* (2013.01)

(58) Field of Classification Search
USPC ................................................ 600/587, 595
See application file for complete search history.

(56) References Cited

U.S. PATENT DOCUMENTS

| | | | |
|---|---|---|---|
| 4,771,792 A * | 9/1988 | Seale ................. | A61B 5/02133 600/552 |
| 4,817,628 A | 4/1989 | Zealear et al. | |
| 4,836,218 A * | 6/1989 | Gay et al. ...................... | 600/586 |
| 5,293,879 A | 3/1994 | Vonk et al. | |
| 5,913,310 A | 6/1999 | Brown | |
| 6,053,866 A | 4/2000 | McLeod | |
| 6,561,992 B1 | 5/2003 | Eberhart et al. | |
| 6,878,121 B2 | 4/2005 | Krausman et al. | |
| 7,983,872 B2 | 7/2011 | Makino et al. | |
| 8,187,209 B1 | 5/2012 | Giuffrida | |
| 2002/0156392 A1 | 10/2002 | Arai et al. | |
| 2004/0220493 A1 | 11/2004 | Teicher et al. | |
| 2005/0075553 A1 | 4/2005 | Sakai et al. | |
| 2005/0234309 A1* | 10/2005 | Klapper ............... | A61B 5/1101 600/300 |
| 2005/0240086 A1 | 10/2005 | Akay | |
| 2006/0287614 A1 | 12/2006 | Hogan et al. | |
| 2008/0033259 A1 | 2/2008 | Manto et al. | |
| 2008/0045804 A1 | 2/2008 | Williams | |
| 2008/0053253 A1 | 3/2008 | Moore et al. | |
| 2009/0062696 A1 | 3/2009 | Nathan et al. | |
| 2009/0326419 A1* | 12/2009 | Gonzalez Rojas et al. .. | 600/587 |
| 2010/0030119 A1 | 2/2010 | McNames et al. | |

FOREIGN PATENT DOCUMENTS

| | | |
|---|---|---|
| EP | 1994883 A1 | 11/2008 |
| EP | 2660745 A2 | 11/2013 |
| JP | 2004136074 A | 5/2004 |
| JP | 2004261525 A | 9/2004 |
| JP | 2005-152053 | 3/2005 |
| JP | 2007075428 A | 3/2007 |
| WO | 9739677 A1 | 10/1997 |
| WO | 9952038 A1 | 10/1999 |
| WO | 03053245 A2 | 7/2003 |
| WO | 03063876 A2 | 8/2003 |
| WO | 2004/008427 | 1/2004 |
| WO | 2004008427 | 1/2004 |
| WO | 2004/084725 | 10/2004 |
| WO | 2004084725 | 10/2004 |
| WO | 2005120347 A1 | 12/2005 |
| WO | 2006/088415 A1 | 8/2006 |
| WO | 2006088415 A1 | 8/2006 |
| WO | 2006/105621 | 10/2006 |
| WO | 2006105621 | 10/2006 |
| WO | 2007105648 A1 | 9/2007 |
| WO | 2007136677 A2 | 11/2007 |
| WO | 2008/037260 | 4/2008 |
| WO | 2008037260 | 4/2008 |
| WO | 2009149520 A1 | 12/2009 |
| WO | 2012129636 A1 | 10/2012 |
| WO | 2013012625 A1 | 1/2013 |
| WO | 2014131090 A1 | 9/2014 |

OTHER PUBLICATIONS

Caligiuri et al., "A quantitative study of levodopa-induced dyskinesia in Parkinson's disease", J. Neural Transm, 1993, vol. 6, pp. 89-98.
Gresty et al., "Postural and Resting Tremors in Parkinson's Disease", Advances in Neurology, 1984, vol. 40, pp. 361-364.
Kraus et al., "Assessment of symptoms of Parkinson's disease by apparative methods", J. Neural. Trans., 1987 (Supp) vol. 25, pp. 89-96.
Manson et al., "An ambulatory dyskinesia monitor", J. Neurol. Neurosurg Psychiatry, 2000, vol. 68, pp. 196-201.
Obeso et al., "Motor complications associated with chronic levodopa therapy in Parkinson's disease", Neurology, Nov. 1989, vol. 38, Suppl 2, pp. 11-19.
Tryon et al., "Accelerometric Assessment of Tardive Dyskinesia", Am J. Phychiatry, 1987, vol. 144, pp. 1584-1587.
Wade et al., "A Normative Study of Postural Tremor of the Hand", Arch Neurol, Jun. 1982, vol. 39, pp. 358-362.
Eus J.W. Van Someren et al., "New Actigraph for Long-Term Tremor Recording", Movement Disorders, vol. 21, No. 8, 2006, pp. 1136-1143.
JJ van Hilten et al., A new approach in the assessment of motor activity in Parkinson's disease, Journal of Neurology, Neurosurgery, and Psychiatry, 1991, 54, pp. 976-979.
Jorrit Ivar Hoff, "Ambulatory accelerometry in Parkinson's disease", University of Leiden (Doctoral Thesis), Sep. 30, 2005, Retrieved from: http://openaccess.leidenuniv.nl/bitstream/handle/1887/3756/Proefschrift2.pdf?sequence=1.
Van Hilten et al., "Quantitative Assessment of Parkinsonian Patients by Continuous Wrist Activity Monitoring", Clinical Neuropharmacology, 1993, vol. 16, No. 1., pp. 36-45.
Keijsers et al., "Automatic Assessment of Levodopa-Induced Dyskinesias in Daily Life by Neural Networks", Movement Disorders, vol. 18, No. 1, 2003, pp. 70-80.
Tremorwatch, Printed from http://www.salusa.se/Filer/produktinfo/Akivitet/tremorwatch.pdf, printed Aug. 4, 2011, 2 pgs.
"Kinesia movement Disorder Assessment System", Wireless Gyroscope, Wireless Accelerometer, printed Aug. 4, 2011 from http://www.clevemed.com/kinesia/hardware.shtml, 2 pgs.
"SHIMMER—Sensing Health with Intelligence, Modularity, Mobility, and Experimental Reusability", printed Aug. 4, 2010 from http://www.eecs.harvard.edu/~konrad/projects/shimmer/references/SHIMMER_HWGuide_REV1P3.pdf, 15 pgs.
Andreeva et al., "Application EMGs spectral analysis method for the objective diagnosis of different clinical forms of Parkinson's disease", Electromyogr. Clin. Neurophysiol., 1996, vol. 36, pp. 187-192.
Beuter et al., "The measurement of tremor using simple laser systems", Journal of Neuroscience Methods, 1994, vol. 53, pp. 47-54.
Boyce et al., "Induction of Chorea and Dystonia in Parkinsonian Primates", Movement Disorders, 1990, vol. 5, No. 1, pp. 3-7.
Caligiuri et al., "A quantitative study of levodopa-induced dyskinesia in Parkinson's disease", J. Neural Transm. 1993, vol. 6, pp. 89-98.
Caligiuri et al., "Instrumental Assessment of Lingual Motor Instability in Tardive Dyskinesia", Neuropsychopharmacology, 1989, vol. 2, No. 4, pp. 309-312.
Cleeves et al., "Assessment of Rest Tremor in Parkinson's Disease", Advances in Neurology, 1986, vol. 45, pp. 349-352.
Eichhorn et al., "Computational Analysis of Open Loop Handwriting Movements in Parkinson's Disease: A Rapid Method to Detect Dopamimetic Effects", Movement Disorders, 1996, vol. 11, No. 3, pp. 289-297.
Elble, "Gravitational artifact in accelerometric measurements of tremor", Clinical Neurophysiology, 2005, vol. 116, pp. 1638-1643.
Elble et al., "Quantification of tremor with a digitizing tablet", Journal of Neuroscience Methods, 1990, vol. 32, pp. 193-198.
Gerlach, "Relationship Between Tardive Dyskinesia, I-Dopa-Induced Hyperkinesia and Parkinsonism", Psychopharmacology, 1977, vol. 51, pp. 259-263.
Ghika et al., "Portable System for Quantifying Motor Abnormalities in Parkinson's Disease", IEEE Transactions on Biomedical Engineering, Mar. 1993, vol. 40, No. 3, pp. 276-283.
Goetz et al., "Movement Disorder Society-Sponsored Revision of the Unified Parkinson's Disease Rating Scale (MDS-UPDRS): Scale Presentation and Clinimetric Testing Results", Movement Disorders, 2008, vol. 23, No. 15, pp. 2129-2170.

(56) References Cited

OTHER PUBLICATIONS

Goetz et al., "The Unfied Parkinson's Disease Rating Scale (UPFRS): Status and Recommendations, Movement Disorder Society Task Force on Rating Scales for Parkinson's Disease", Movement Disorders, 2003, vol. 18, No. 7, pp. 738-750.

Goetz et al., "Utility of an Objective Dyskinesia Rating Scale for Parkinson's Disease: Inter- and Intrarater Reliability Assessment", Movement Disorders, 1994, vol. 9, No. 4, pp. 390-394.

Gonce et al., "Clinical Neurophysiological Assessment of Parkinson's Disease", Advances in Neurology, 1984, vol. 40, pp. 365-373.

Gresty et al., "Postural and Resting Tremors in Parkinson's Disease", Advances in Neurology, 1984, vol. 40, pp. 361-364.

Gresty et al., "Spectral analysis of tremor: understanding the results", Journal of Neurology, Neurosurgery and Psychiatry, 1990, vol. 53, pp. 976-981.

Hadar et al., "Is Parkinsonian Arm Tremor a Resting Tremor?", Eur. Neurol., 1993, Vo. 33, pp. 221-228.

Hilten, J J V. et al., "A new approach in the assessment of motor activity in Parkinson's disease", Journal of Neurology, Neurosurgery, and Psychiatry 1991;54:976-979, 1991, 4.

Hoff, Jorrit I., "Ambulatory accelerometry in Parkinson's disease", 1969, 111.

Hughes et al., "Accuracy of clinical diagnosis of idiopathic Parkinson's Disease: a clinico-pathological study of 100 cases", Journal of Neurology, Neurosurgery, and Psychiatry, 1992, vol. 55, pp. 181-184.

Hughes et al., "Motor response to levodopa in patients with parkinsonian motor fluctuations: a follow-up study over three years", Journal of Neurology, Neurosurgery, and Psychiatry, 1994, vol. 57, pp. 430-434.

Johnels et al., "Disability profiles and objective quantitative assessment in Parkinson's disease", Acta Neurol. Scand., 1989, vol. 79, pp. 227-238.

Keijsers, Noel L., "Online monitoring of dyskinesia in patients with Parkinson's disease", Engineering in Medicine and Biology Magazine, IEEE, vol. 22, Issue 3, May-Jun. 2003, pp. 96-103.

Kraus et al., "Assessment of symptoms of Parkinson's disease by apparative methods", J. Neural. Trans., 1987 (Sup) vol. 25, pp. 89-96.

Lorincz et al., "Wearable Wireless Sensor Network to Assess Clinical Status in Patients with Neurological Disorders", IPSN 07, Apr. 25-27, 2007, pp. 563-564.

Manson et al., "An ambulatory dyskinesia monitor", J. Neurol. Neurosurg. Psychiatry, 2000, vol. 68, pp. 196-201.

Marconi et al., "Levodopa-Induced Dyskinesias in Parkinson's Disease Phenomenology and Pathophysiology", Movement Disorders, 1994, vol. 9, No. 1, pp. 2-12.

Marsden, "Slowness of Movement in Parkinson's Disease", Movement Disorders, 1989, vol. 4, suppl. 1, pp. S26-S37.

Marsden et al., "Assessment of Extrapyramidal Disorders", Br. J. clin. Pharmac., 1981, vol. 11, pp. 129-151.

McColl et al., "Motor Response to Levodopa and the Evolution of Motor Fluctuations in the First Decade of Treatment of Parkinson's Disease", Movement Disorders, 2002, vol. 17, No. 6, pp. 1227-1234.

Moore et al., "Long-term monitoring of gait in Parkinson's disease", Gait & Posture, 2007, vol. 26, pp. 200-207.

Nutt, "Levodopa-induced dyskinesia: Review, observations and speculations", Neurology, 1990, vol. 40, pp. 340-345.

Nutt et al., "Short- and Long-Duration Responses to Levodopa During the First Year of Levodopa Therapy", Annals of Neurology, Sep. 1997, vol. 42, No. 3, pp. 349-355.

Obeso et al., "Motor complications associated with chronic levodopa therapy in Parkinson's disease", Neurology, Nov. 1989, vol. 38, Suppl. 2, pp. 11-19.

O'Boyle et al., "The Accuracy and Precision of Time of Self-Paced, Repetitive Movements in Subjects with Parkinson's Disease", Brain, 1996, vol. 119, pp. 51-70.

Pahwa et al., "Defining Parkinson's Disease and Parkinsonism", Etiology of Parkinson's Disease, 1995, pp. 1-54.

Phillips et al., "characteristics of Handwriting of Patients with Huntington's Disease", Movement Disorders, 1994, vol. 9, No. 5, pp. 521-530.

Post et al., "Unified Parkinson's Disease Rating Scale Motor Examination: Are Ratings of Nurses, Residents in Neurology, and Movement Disorders Specialists Interchangeable?", Movement Disorders, 2005, vol. 20, No. 12, pp. 1577-1584.

Redmond et al., "Observations on the design and specification of wrist-worn human activity monitoring system", Behavior Research Methods, Instruments & Computer, 1985, vol. 17, No. 6, pp. 659-669.

Salarian et al., "An Ambulatory System to Quantify Bradykinesia and Tremor in Parkinson's Disease", Proc. of the 4th Annual IEEE Conf. on Information Technology Applications in Biomedicine, pp. 35-38.

Schuurman et al, "A comparison of neuropsychological effects of thalamotomy and thalamic stimulation", Neurology, 2002, vol. 59, pp. 1232-1239.

Sheridan et al., "Movement Variability and Bradykinesia in Parkinson's Disease", Brain, 1990, vol. 113, pp. 1149-1161.

Sherrill et al., "Advanced Analysis of Wearable Sensor Data to Adjust Medication Intake in Patients with Parkinson's Disease", Proceedings of the 2nd International IEEE EMBS Conference on Neural Engineering, Mar. 2005, pp. v-viii.

Someren, E.J.W. V. et al., "Ambulatory monitoring of tremor and other movements before and after thalamotomy: a new quantitative technique", Journal of the Neurological Sciences, 1993, 8.

Someren, J.W. V. et al., "A New Actigraph for Long-Term Registration of the Duration and Intensity of Tremor and Movement", IEEE Transactions on Biomedical Engineering vol. 45, No. 3, Mar. 1998, Mar. 1998, 10.

Someren, J.W. V. et al., "Actigraphic Monitoring of Movement and Rest-Activity Rhythms III Aging, Alzheimer's Disease, and Parkinson's Disease", IEEE Transactions on Rehabilitation Engineering, vol. 5, No. 4, Dec. 1997, 5.

Someren, J.W. V. et al., "New Actigraph for Long-Term Tremor Recording", Movement Disorders vol. 21 No. 8, 2006, 2006, 8.

Spieker et al., "Validity of Long-Term Electromyography in the Quantification of Tremor", Movement Disorders, 1997, vol. 12, No. 6, pp. 985-991.

Stochl et al., "On the Structure of Motor Symptoms of Parkinson's Disease", Movement Disorders, 2008, vol. 23, No. 9, pp. 1307-1315.

Tryon et al., "Accelerometric Assessment of Tardive Dyskinesia", Am J. Psychiatry, 1987, vol. 144, pp. 1584-1587.

Van Hilten, et al., "Quantitative Assessment of Parkinsonian Patients by Continuous Wrist Activity Monitoring", Clinical Neuropharmacology, 1993, vol. 16, No. 1, pp. 36-45, 1993, 10.

Van Hilten et al., "Bradykinesia and hypokinesia in Parkinson's disease: what's in a name?", J. Neural Transm, 1998, vol. 105, pp. 229-237.

Veltink et al., "Towards a New Method for Kinematic Quantification of Bradykinesia in Patients with Parkinson's Disease Using Triaxian Accelometry", IEEE-EMBC and CMBEC Theme 5: Neuromuscular Systems/Biomechanics, 1995, pp. 1303-1304.

Wade et al., "A Normative Study of Postural Tremor of the Hand", Arch Neurol. Jun. 1982, vol. 39, pp. 358-362.

Weitzman et al., "Quantification of Chorea in Huntington's Disease by Power Spectral Analysis", Diseases of the Nervous System, 1976, pp. 264-268.

Yanagisawa et al., "Bradykinesia in Parkinson's Disease: Disorders of Onset and Execution of Fast Movement", Eur. Neurol. 1989, vol. 29 (suppl. 1), pp. 19-28.

Yanagisawa et al., "Pathophysiology of Involuntary Movements in Parkinson's Disease", Eur. Neurol., 1987, vol. 26, Suppl. 1, pp. 30-40.

Carboncini et al., "The Relation Between EMG Activity and Kinematic Parameters Strongly Supports a Role of the Action Tremor in Parkinsonian Bradykinesia", Movement Disorders vol. 16, No. 1, 2001, pp. 47-57 © 2001 Movement Disorder Society.

May 5, 2015—(PCT) International Search Report—App. PCT/AU2015/050084.

(56) References Cited

OTHER PUBLICATIONS

Sep. 16, 2016 (EP) Extended European Search Report—App. 14756592.3.
Mar. 27, 2014 (PCT)—International Search Report and Written Opinion—App. PCT/AU2014/000191.
Motor Inhibition and Cognitive Flexibility in Obssessive-Compulsive Disorder and Trichotillomania, Samuel R. Chamberlain, M.A., et al., Am. J. Psychiatry, Jul. 2006:163: pp. 1282-1284.
Impulse inhibition in people with Internet addiction disorder; Electrophysiological evidence from a Go/No Go study, Guangheng Dong, et al., Nueoscience Letters 485, © 2010 Elsevier Ireland Ltd., pp. 138-142.
Cognitive dysfunction in childhood-onset pathologic skin picking, Jon E. Grant, et al., Journal of Obsessive-Compulsive and Related Disorders, © 2012 Elsevier Ltd., pp. 73-76.

* cited by examiner

DETECTION OF HYPOKINETIC AND HYPERKINETIC STATES

CROSS-REFERENCE TO RELATED APPLICATIONS

The present application claims priority from Australian Provisional Patent Application No 2008902982 filed on 12 Jun. 2008 and Australian Provisional Patent Application No 2009902616 filed on 9 Jun. 2009, the content of which is incorporated herein by reference.

TECHNICAL FIELD

This invention relates to analysis of kinetic state of a person by monitoring motion symptoms to detect bradykinesia and/or dyskinesia or hyperkinesia.

BACKGROUND OF THE INVENTION

A range of diseases, medications, trauma and other factors can lead to a person having motion symptoms such as dyskinesia, in which the person is in a hyperkinetic state, or bradykinesia, in which the person is in a hypokinetic state.

For example, bradykinesia is a key manifestation of Parkinson's disease. L-Dopa, or Levodopa, is often administered to patients having Parkinson's disease, and can have the effect of causing the patient to become dyskinetic for a period of time after administration. As Parkinson's disease progresses, the half life of L-Dopa shortens and the effective dose range decreases, making dosage control extremely difficult and complex. This is commonly managed by increasing the dose frequency, sometimes by as much as ten doses each day in an attempt to control symptoms and enable the patient to have a reasonable quality of life. Thus, patients with Parkinson's disease may experience periods of bradykinesia, dyskinesia and normal motor function several times a day and throughout the course of a single dose of L-Dopa.

Even if a satisfactory dosage regime is reached at one point in time, the progressive nature of Parkinson's disease means that neurologists must regularly review a patient's symptoms in order to effectively control the patient's ongoing treatment dosage. Without objective and ongoing monitoring it is very difficult for physicians to avoid prescribing either an excessive dose which overly increases episodes of dyskinesia, or an inadequate dose which does not prevent episodes of bradykinesia. Furthermore there is no objective measure to say whether a change in dose was effective in improving symptoms.

From clinical observation, skilled neurologists can usually detect the existence of bradykinesia and dyskinesia. In one approach, the observing physician gives a score in the range of 0 to 20 to indicate the severity of the observed episode. FIG. 1 shows scores given by three neurologists, with each plotted point representing the scores given by two neurologists when observing a single dyskinetic episode. Scores for Neurologist 1 (triangles) and Neurologist 3 (circles) are plotted against scores from Neurologist 2. As is evident, the subjective nature of this scoring approach leads to considerable variation. In one extreme example, Neurologist 2 scored one dyskinetic episode as being of severity 10 (being quite severe when noting that the highest score ever given by Neurologist 2 was a 13), whereas Neurologist 3 scored the same episode as being of severity 0 (no dyskinesia observed). Thus, while physicians can usually detect dyskinesia and other kinetic states during observation, these states are not easily quantified, making dosage control very subjective.

Further, clinical observation typically only occurs over a short period of patient attendance, usually of the order of tens of minutes, once every 6 or 8 weeks. Fluctuations in kinetic state throughout the day and from one day to the next significantly complicate attempts at assessing the patient's kinetic state. Clinicians often rely on the patient's recollection and/or written diaries to gain an understanding of the ongoing kinetic state of the patient between clinical appointments. However patients can rarely give objective scores, and the effect of a kinetic episode itself can often make it difficult for a patient to make any record whatsoever of the nature of and timing of motor fluctuations.

Another common symptom, of Parkinson's Disease for example, is tremor. Parkinsonian tremor is slower than most forms of tremor with a frequency of 4-6 cycles per second. Compared with other elements of movement, tremor consists of oscillations of relatively few frequency components. On spectral analysis, it appears as a discrete peak in a narrow frequency range (4-6 Hz), usually clearly above the frequency range of normal movement (less than 4 Hz). Tremor has been the subject of numerous studies and is particularly amenable to study with spectral analysis. Tremor is relatively easy to detect because it is a continuous repetitive movement, giving a sinusoidal signature, which is simple to distinguish from normal human motions which are rarely so continuous. Tremor is far less a problem in management of Parkinson's Disease than dyskinesia and bradykinesia. Attempts have been made to infer a person's bradykinetic state from measurements of tremor, in an attempt to regulate medication. However for many patients there is not a close correlation between tremor and bradykinesia, making it likely that medication will be inaccurately administered using this technique.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention provides an automated method of determining a kinetic state of a person, the method comprising:

obtaining data from an accelerometer worn on an extremity of the person; and processing the data to determine a measure for the kinetic state, the kinetic state being at least one of bradykinesia, dyskinesia, and hyperkinesia.

According to a second aspect, the present invention provides a device, for determining a kinetic state of a person, the device comprising:

a processor configured to process data obtained from an accelerometer worn on an extremity of the person and to determine from the data a measure for the kinetic state, the kinetic state being at least one of bradykinesia, dyskinesia, and hyperkinesia.

According to a third aspect, the present invention provides a computer program product comprising computer program means to make a computer execute a procedure for determining a kinetic state of a person, the computer program product comprising:

computer program code means for obtaining data from an accelerometer worn on an extremity of the person; and computer program code means for processing the data to determine a measure for the kinetic state, the kinetic state being at least one of bradykinesia, dyskinesia, and hyperkinesia.

Notably, the present invention thus provides for a determination to be made as to a kinetic state of a person based on measurements obtained from a single accelerometer worn on an extremity of the person. In this specification the term kinetic state is defined to be a movement disorder state. This invention recognises that a single sensor worn on an extremity provides adequate movement-related data to enable a determination of a state of bradykinesia and/or dyskinesia or hyperkinesia to be made. Embodiments of the invention may thus be particularly suitable for frail, elderly or disabled persons for whom fitting more than a single sensor becomes impractical. In some embodiments the accelerometer is worn below the elbow, such as on the wrist. In other embodiments the sensor may be worn below the knee, such as on the ankle.

Further, the present invention provides for an automated determination of a kinetic state which is at least one of bradykinesia and dyskinesia, thus providing a technique which does not rely on a potentially inaccurate inference of bradykinesia based on a measure of tremor.

In preferred embodiments, the accelerometer data is processed in order to determine both a measure for bradykinesia and a measure for dyskinesia.

Bradykinesia

In some embodiments in which a measure of bradykinesia is determined, digital data from the accelerometer is band pass filtered to extract data for a band of interest. The band of interest may have a lower end cut off frequency which is selected to remove DC. The lower end cut off frequency for example may be in the range of 0.05 Hz to 1 Hz, preferably being 0.2 Hz. The band of interest may have an upper end cut off frequency which is selected to eliminate high frequency components which in general do not arise from normal human motions. The upper end cut off frequency for example may be in the range of 3 Hz to 15 Hz, preferably being 4 Hz. An upper cut off of around 4 Hz may be beneficial in avoiding or minimising of the influence of tremor, which is usually over 4 Hz.

Additionally or alternatively, in some embodiments in which a measure of bradykinesia is determined, a time block or "bin" of digital acceleration data is extracted from the time series of data and considered in isolation, with each bin being of a time duration which is selected to be small enough that relatively regular measures of bradykinesia are determined, while being long enough to provide a reasonable likelihood of a significant movement by the person during that bin. For example, the bin duration may be in the range of two seconds to 60 minutes, more preferably being in the range of 15 seconds to four minutes, and most preferably being in the range of 30 seconds to two minutes.

Additionally or alternatively, in some embodiments in which a measure of bradykinesia is determined, the digital data is searched for a maxima, preferably using a moving mean having a window length which is a fraction of the duration of a normal human motion, for example the window length of the moving mean may be in the range of 0.02 seconds to 30 seconds, and may be substantially 0.2 seconds. The window in which the data is found to have the highest mean is taken to represent the movement of peak acceleration by the person. Such embodiments recognise that a person in a normal kinetic state generally has movements of higher peak acceleration than a bradykinetic person, and that the peak acceleration is thus an indicator by which a bradykinetic state may be detected and quantified. In embodiments assessing data bins, for bin i the highest mean is referred to as PKi, being the window of peak acceleration. A threshold may be applied whereby values of PKi below the threshold are excluded to allow for the possibility that a bradykinetic person and a normally kinetic person may each simply remain still for some bins.

Additionally or alternatively, in some embodiments in which a measure of bradykinesia is determined, a sub-bin comprising a plurality of data points both before and after a peak acceleration are obtained. The sub-bin preferably comprises a number of data points which is a power of two, and the sub-bin is preferably symmetrically positioned about the peak acceleration. The sub-bin preferably comprises data points obtained over a period of time which is substantially the same as the duration of a normal single human motion, for example the duration of the sub-bin may be in the range of 0.5 seconds to 30 seconds, more preferably in the range of 1 second to 3 seconds, and for example may be substantially 2.56 seconds. The sub-bin is further preferably a small fraction of the length of an associated bin, if any. A spectral analysis of the sub-bin is preferably conducted, for example by performing a Fast Fourier Transform on the data of the sub-bin to obtain sub-band spectral measures. The sub-bands may be of a width which is around one fourth of a band of interest. The sub-bands may be of a width in the range of 0.1 Hz to 2 Hz, more preferably in the range of 0.6 Hz to 1 Hz, and may be substantially 0.8 Hz. The sub-bands may be overlapping in the frequency domain, for example eight partially overlapping sub-bands may be considered.

Such embodiments thus provide for spectral components of the single movement of peak acceleration to be obtained, recognising that if the person's peak movement has strong low frequency components this is indicative of bradykinesia. Some embodiments may thus identify which single sub-band has greatest power and give a stronger indication of the presence of bradykinesia when a low frequency sub-band has greatest power. Additionally or alternatively a weighting may be applied to some or all of the sub-band spectral measures to produce a weighted mean spectral power $MSP_i$ such that a greater indication of bradykinesia is given when the maximum ($MSP_i$) is small and exists in lower frequency sub-bands, and a lesser indication of bradykinesia is given when the maximum ($MSP_i$) is high and exists in higher frequency sub-bands.

Additionally or alternatively, in some embodiments in which a measure of bradykinesia is determined, a plurality n of consecutive bins may be considered, a PKi and MSPi determined for each bin, and from across the n bins selecting the largest value of PKi ($PK_{i,max}$) and selecting the largest value of MSPi ($MSP_{i,max}$). A bradykinesia score BK may then be computed as:

$$BK = PK_{i,max} \times MSP_{i,max}$$

Alternatively, a bradykinesia score may be computed as:

$$BK = A \times \log_e(PK_{i,max} \times MSP_{i,max}) - B$$

where A, c and B are selectable tuning constants. In a non limiting example A=16.667, n=10 and B=116.667. Such embodiments recognise that, if a person is remaining still, individual bins may carry little information to enable differentiation between a normally kinetic person and a bradykinetic person. Consideration of a sequence of bins increases the likelihood that actual movements are being considered.

Additional or alternative embodiments may provide for the BK score to be influenced by whether the person goes for long periods without movement. Such embodiments recognise a key differentiating factor between normally kinetic persons and bradykinetic persons, which is that normally kinetic persons rarely if ever remain completely motionless for any significant period of time, whereas bradykinetic persons can remain motionless for significant periods. Such embodiments might for example consider a threshold acceleration value of the $PK_i$ of multiple bins, such as the mode of the $PK_i$ values, which will take a small value. Should the $PK_i$ of the person go for a long period (referred to as a quiet time or QT) without exceeding the threshold, this may in such embodiments be taken to indicate a bradykinetic state. For example, the bradykinesia score might be computed as:

$$BK = A \times \log_c(PK_{i,max} \times MSP_{i,max})/QT^m - B$$

such that a large QT reduces the BK score, thereby more strongly indicating bradykinesia. The value of m is preferably greater than or equal to 1, such that long of periods QT more strongly influence the BK score.

It is noted that such embodiments produce a BK score which has a larger value for normally kinetic persons and a smaller value closer to zero for bradykinetic persons, consistent with common clinical subjective measures.

In another embodiment, QT may be used as an additional indicator of BK in its own right. A large QT would be very BK.

A moving mean of multiple consecutive BK scores may be output to smooth the results. In some embodiments the measure of bradykinesia may be determined repeatedly over time, for example the measure may be determined every few minutes. In such embodiments, a cumulative bradykinesia score comprising a sum of the individual measures may be determined in order to provide a cumulative indication of the kinetic state. For example the cumulative score may be determined over the course of a single dose of L-dopa, or over the course of a day.

Some embodiments of the invention thus recognise that bradykinetic movements have lower acceleration and velocity, and that the low frequency, amplitude, velocity and acceleration of bradykinetic movements is manifested in a spectral analysis by a relative preponderance of low frequencies and reduced power in all frequencies.

Dyskinesia

In some embodiments in which a measure of dyskinesia is determined, the digital data from the accelerometer is band pass filtered to extract data for a band of interest. The band of interest may have a lower end cut off frequency, which is selected to remove DC components, for example being in the range of 0.05 Hz to 2 Hz, preferably being 1 Hz. The band of interest may have an upper end cut off frequency, which is selected to eliminate higher frequency components which in general do not arise from normal human motions, for example being in the range of 3 Hz to 15 Hz, preferably being 4 Hz. An upper cut off of around 4 Hz may be beneficial in avoiding or minimising the influence of tremor which is usually over 4 Hz.

Additionally or alternatively, in some embodiments in which a measure of dyskinesia is determined, a time block or "bin" of digital acceleration data is extracted from the time series of data and considered in isolation, with each bin being of a time duration which is selected to be small enough that relatively regular measures of dyskinesia are determined, while being long enough to provide a reasonable likelihood that a normally kinetic person will have periods of little or no movement during that bin. For example the bin duration may be in the range of ten seconds to 10 minutes, more preferably being in the range of 30 seconds to four minutes, and most preferably being substantially two minutes. Such embodiments recognise that a differentiating factor between a normally kinetic person and a dyskinetic person is that a normally kinetic person will have periods of little or no movement, whereas a dyskinetic person generally can not keep still and thus has few periods of little or no movement.

Additionally or alternatively, in some embodiments in which a measure of dyskinesia is determined, the data may be compared to a threshold value and a period or proportion of time for which the data remains below the threshold may be determined. Such a measure relates to the period or proportion of time for which the person has reduced movement, and is referred to herein as the time of reduced movement ($T_{RM}$). The threshold value may be the mean value of the data. A moving mean of the data may be what is compared to the threshold, to reduce the effects of noise. For example a window length of the moving mean may be in the range of 0.5 seconds to 4 seconds, preferably substantially one second. A $T_{RM}$ measure produced in such embodiments will be small for dyskinetic persons as they have few periods of no movement, but will be larger for normally kinetic persons, thereby enabling dyskinesia to be detected and quantified.

Additionally or alternatively, in some embodiments in which a measure of dyskinesia is determined, the data may be compared to a threshold value and a power measure of data which falls below the threshold may be determined. Such embodiments recognise that for a dyskinetic person data below the threshold will have a greater power than for a normally kinetic person, as a dyskinetic person will rarely be truly motionless. The threshold may be the mean value of the data, which will take a higher value for dyskinetic persons and lead to a higher power of data below the threshold, thereby enhancing the ability to detect and quantify dyskinesia. The power measure of the data which falls below the measure may comprise the mean spectral power ($SP_{RM}$) obtained by performing a Fast Fourier Transform on the data below the threshold. The root-mean-square (RMS) value of the $SP_{RM}$ may be taken to obtain $SP_{RM,RMS}$.

Additionally or alternatively, in some embodiments in which a measure of dyskinesia is determined, a variance (VAR) of the frequency components of the data may be obtained. Such embodiments recognise that dyskinesia often yields movements at a wide range of frequencies leading to a large VAR, whereas a normally kinetic person tends to move at a similar speed for most motions leading to a small VAR. The VAR thus provides a further measure by which dyskinesia may be detected and quantified.

In some embodiments in which a measure of dyskinesia is determined, a dyskinesia score might be computed as:

$$DK = A \times \log_c(SP_{RM}/T_{RM})$$

Additionally or alternatively, in some embodiments in which a measure of dyskinesia is determined, a dyskinesia score might be computed as:

$$DK = A \times \log_c(Acc \times SP_{RM}/T_{RM})$$

Additionally or alternatively, in some embodiments in which a measure of dyskinesia is determined, a dyskinesia score might be computed as:

$$DK = A \times \log_c(RMS_{RM}/T_{RM})$$

where A, and c are selectable tuning constants, $T_{RM}$ is the time of reduced movement and $RMS_{RM}$ is the root mean-square value of the accelerometer data below the threshold value.

Additionally or alternatively, in some embodiments in which a measure of dyskinesia is determined, a dyskinesia score might be computed as:

$$DK = A \times \log_c(VAR/T_{RM})$$

Additionally or alternatively, in some embodiments in which a measure of dyskinesia is determined, a dyskinesia score might be computed as:

$$DK = A \times \log_c(VAR \times SP_{RM}/T_{RM})$$

As $SP_{RM}$, $SP_{RM,RMS}$, VAR and Acc are large for dyskinetic persons, and $T_{RM}$ is small for dyskinetic persons, the above scores indicate dyskinesia with a high number, consistent with common clinical subjective measures.

A moving mean of multiple consecutive DK scores may be output to smooth the results. In some embodiments the measure of dyskinesia may be determined repeatedly over time, for example the measure may be determined every few minutes. In such embodiments, a cumulative dyskinesia score comprising a sum of the individual measures may be determined in order to provide a cumulative indication of the kinetic state. For example the cumulative score may be determined over the course of a single dose of L-dopa, or over the course of a day.

Some embodiments of the invention thus recognise that dyskinetic movements have greater power, increased amplitude and are of a continuous relentless quality.

In some embodiments, the data is processed to produce both a measure of bradykinesia and a measure of dyskinesia. Such embodiments recognise that a person may suffer both bradykinesia and dyskinesia simultaneously or in close succession and that each state can be independently quantified from the data returned by the accelerometer.

Thus, some embodiments of the present invention provide for objectively detecting and quantifying bradykinetic and/or dyskinetic states, which is of importance in assessing the effect of therapeutic agents, both in clinical trials and in the normal clinical setting, especially to guide use of disease modifying interventions. These embodiments achieve this, even where kinetic symptoms fluctuate, by taking measurements substantially continuously or frequently throughout the day. Moreover, rather then relying on subjective measures of the patient or neurologist, embodiments of the invention provide for an objective measure so that an automated comparative analysis can be undertaken over a longer period, such as over a 24 hour period. Such embodiments recognise that a longer period of analysis is beneficial in order to better assess the effect of therapeutic agents such as L-Dopa.

In some embodiments the accelerometer is a 3-axis accelerometer giving, for each axis of sensitivity, an output proportional to acceleration along that axis. Each output is preferably sampled to obtain data representing acceleration over time. For example 100 Hz sampling may be used.

In some embodiments of the second aspect of the invention, the device may be a central computing device which is remote from the person and configured to receive data from the accelerometer via a communications network. In such embodiments, the central computing device can be further configured to communicate the determined measure of the kinetic state to a physician or clinician or the like associated with the person.

In other embodiments of the second aspect of the invention, the device may be a body-worn device comprising an accelerometer from which the data is obtained. Such embodiments may further comprise an output means, such as a display, to indicate the determined measure of the kinetic state to the person. In such embodiments the processor of the device may further be configured to use the measure of the kinetic state to update a medication regime of the person and to indicate the updated regime to the person. The medication regime may be updated by altering a dose of medication and/or updating a timing of a dose of medication.

BRIEF DESCRIPTION OF THE DRAWINGS

An example of the invention will now be described with reference to the accompanying drawings, in which.

DESCRIPTION OF THE PREFERRED EMBODIMENTS

Figure 1:
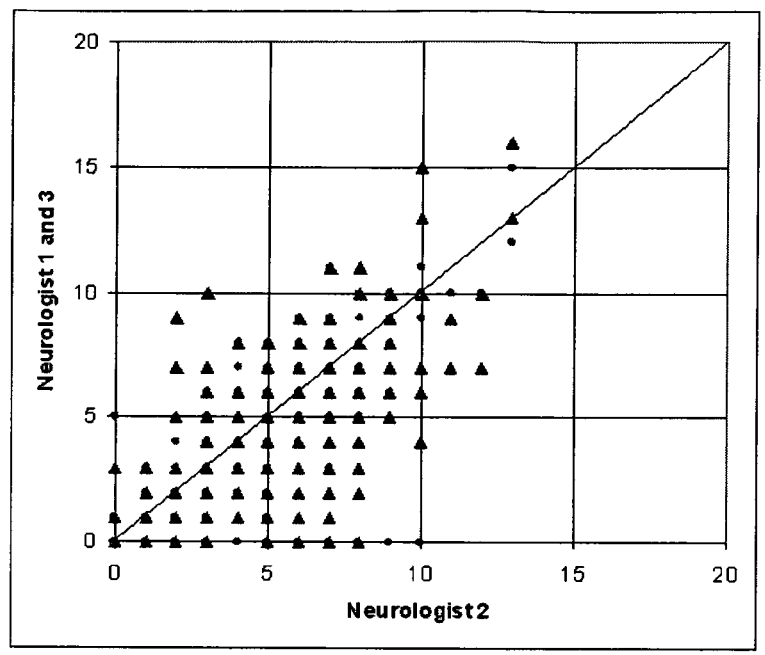
FIG. 1 is a plot of dyskinesia scores given by three neurologists, with each plotted point representing the scores given by two neurologists when observing a single dyskinetic episode.
Figure 2:
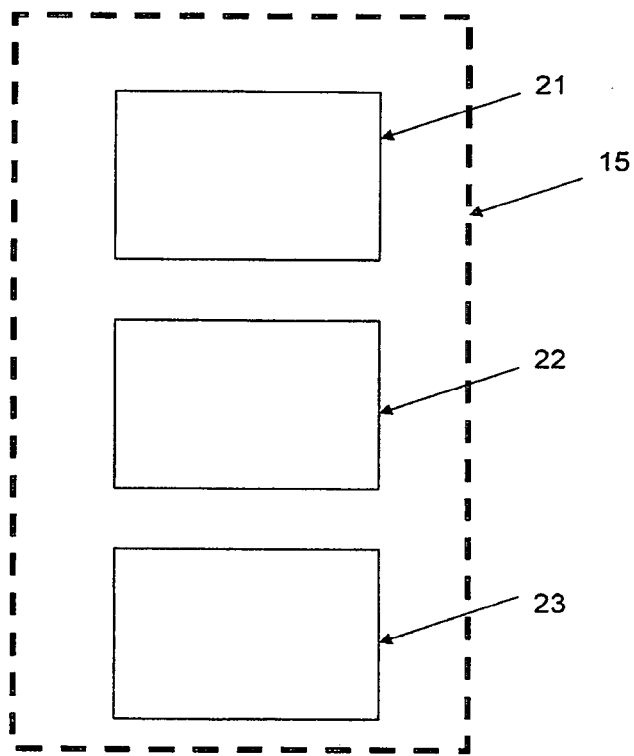
FIG. 2 is a diagrammatic view of a means for detection of various Parkinsonian clinical states in accordance with an embodiment of the invention.
Figure 13:
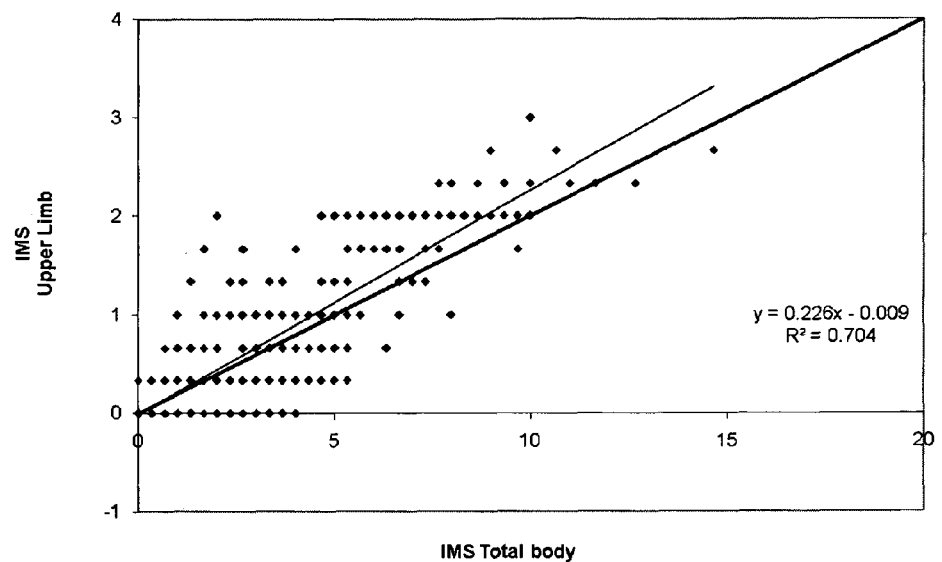
FIG. 13 shows IMS scores for a wrist compared to IMS scores for the whole body.

FIG. 2 is a diagrammatic view of a device 15 for detection of various Parkinsonian or kinetic states in accordance with an embodiment of the invention. The device 15 is wrist mounted which the present inventors have recognised provides a sufficiently accurate representation of the kinetic state of the whole body. For example, IMS scores for a wrist compared to IMS scores for the whole body are shown in FIG. 13, illustrating that the wrist gives adequate kinetic state information. The device 15 comprises three elements for obtaining movement data of a limb of a person. The device 15 comprises a motion monitor 21 in the form of an accelerometer, an assessor 22 for recording and analysis of the received data in a manner that provides an objective determination of bradykinesia and dyskinesia, and an output means 23 for outputting objective determination of bradykinesia or dyskinesia over time periods so as to allow a clinician to prescribe medications or to allow the person to better understand their own kinetic state.

The device 15 is a light weight device which is intended to be worn on the most affected wrist of the person. The device is mounted on an elastic wrist band so as to be firmly supported enough that it does not wobble on the arm and therefore does not exaggerate accelerations. The device is configured to rise away from the person's wrist by a minimal amount so as to minimise exaggeration of movements. The device may be on a wrist band secured by a buckle, whereby the act of unbuckling and removing the device breaks a circuit and informs the logger that the device is not being worn. The patient preferably wears the device for at least 30 minutes prior to taking their first medication for the day, until bedtime. This allows the device to record early morning bradykinesia, which is usually at its worst at this time. The device then goes on to record kinetic responses to all medications for the day.

The accelerometer 21 records acceleration in three axes X, Y, Z over the bandwidth 0-10 Hz, and stores the three channels of data in memory on-board the device. This device has 250 MB of storage so as to allow data to be stored on the device for up to 3 days, after which the device can be provided to an administrator for the data to be downloaded and analysed. Additionally, in this embodiment, when the device is removed each night for patient sleep time, the device is configured to be placed in and interface with a dock so as to have the device transfer the data to the dock which then transmits the data via wireless broadband to analysis servers at the main company (see 114 in FIG. 3). The interface with the dock also provides for batteries of the device to be recharged.

As a wrist-worn device intended for potentially frail persons, the device is of minimal size and weight. Further, for this reason the docking interface is designed such that the device simply falls into place to effect connections of the interface, and provides a very clear feedback that the connection has been made. In one alternative information from the data logger may be transmitted wirelessly by Bluetooth or the like to a PDA (Personal Digital Assistant), kept with the patient to avoid the need for docking to effect data transfer.

Figure 3:
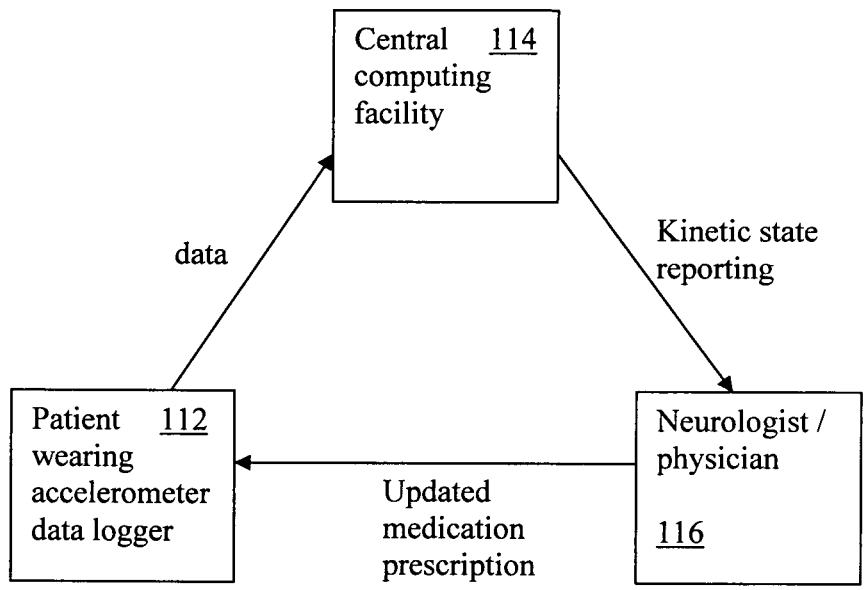
FIG. 3 illustrates kinetic state monitoring and reporting in accordance with one embodiment of the invention.

FIG. 3 illustrates kinetic state monitoring and reporting in accordance with one embodiment of the invention. A patient 112 is wearing the device of FIG. 2. The device 15 logs accelerometer data and communicates it to a central computing facility 114. The computing facility 114 analyses the data using an algorithm (discussed further below), to obtain a time series of scores for the bradykinetic state of the person 112 and a time series of scores for the dyskinetic state of the person. These scores are reported to a neurologist 116 in a format which can be rapidly interpreted by the neurologist to ensure efficient use of the neurologist's time. The report shows major movement categories and is emailed directly to the physician or made available on a website. From this report the patient's medication protocol can be optimised. The neurologist 116 then interprets the kinetic state report and updates a medication prescription of the patient accordingly.

The accelerometer measures acceleration using a uniaxial accelerometer with a measurement range of +/−4 g over a frequency range of 0 to 10 Hz. Alternatively a triaxial accelerometer can be used to provide greater sensitivity.

The device stores data for up to 16 hours per day, for up to 7 days. The stored data is then transferred to the central computing facility 114 manually or by wireless broadband, or via Bluetooth radio to a PDA, or the like. The recording system is thus fully mobile and can be worn at home by the patient.

In this embodiment algorithms are applied to the obtained data by a central computing facility 114 in order to generate a dyskinesia score and a bradykinesia score.

Bradykinesia Scoring Algorithm

The algorithm for producing an automated bradykinesia score (BK) stems from the recognition that bradykinetic subjects have longer intervals between movement and when they do move it is with lower acceleration. Bradykinetic patients thus have a low percentage of time with movement. Normally kinetic persons have a higher percentage of time in which they are moving and a higher peak acceleration of movements. In keeping with presently used subjective measures based on clinical observation, in this algorithm a low BK score indicates more severe bradykinesia, while a high BK score indicates little or no bradykinesia. The bradykinesia scoring algorithm operates on the recorded data in the following steps.

BK1: the data is band-pass filtered to extract components in the range 0.2 to 4 Hz, in order to remove DC, wrist rotation, tremor above 4 Hz, and accidental bumping of the logger and the like.

BK 2: Retrieve a short bin of data at a time, being 30 seconds or 3000 data points per bin in this embodiment. The bin length is long enough to provide a good chance that the person will undertake significant movement within that bin period such that parameters $PK_t$ and $SP_{maxi}$ (described further below) are likely to arise from such a movement.

Steps BK 3 to BK9 are designed to find a maximum acceleration in the bin and the frequency at which this acceleration occurred. This recognises that normal movements have higher accelerations which occur at higher frequencies, while bradykinesia is characterised by lower peak accelerations occurring at lower frequency.

BK3: the $i^{th}$ bin is searched for a maximum acceleration value using a 0.2 second (20 data points) moving mean to eliminate noise. The 0.2 second period with the highest mean is deemed to be the peak acceleration, PKi. Noise may in other embodiments be eliminated by taking a median, or by selecting high values out, or by low pass filtering.

BK4: X points either side of PKi are collected, to create a sub-bin of 2× data points to be used for a FFT. In this embodiment 128 points are taken either side to produce a sub bin of 256 points (2.56 s).

BK5: A FFT is performed on the peak acceleration sub-bin, on the raw accelerometer signal, to find the frequency components present around the PKi.

BK6 : Overlapping 0.8 Hz bands are considered, namely:
A 0.2-1.0 Hz
B 0.6-1.4 Hz
C 1.0-1.8 Hz
D 1.4-2.2 Hz
E 1.8-2.6 Hz
F 2.2-3.0 Hz
G 2.6-3.4 Hz
H 3.0-3.8 Hz The band which contains the maximum mean spectral power SPmaxi is identified.

BK7: The value in each of the eight frequency bins is weighted as follows:
A×0.8
B×0.9
C×1.0
D×1.1
E×1.2
F×1.3
G×1.4
H×1.5

A maximum weighted mean spectral power ($MSP_{MAX}$) is identified from the weighted band values, using a linear look-up function.

BK8: A high MSPmax with high frequencies and high amplitudes is taken to be more likely to indicate a non-bradykinetic state, while a small MSPmax is more likely to indicate bradykinesia.

BK 9: Steps BK3 to BK8 are repeated for each 30 second bin to obtain a series of MSPmax.i values.

BK10: The biggest movements over a group of the analysis bins are identified and recorded. The group of analysis bins may extend over four bins to yield a BK score every 2 minutes, or may extend over six bins to yield a BK score every 3 minutes, for example. The maximum PKi of the group of bins and the largest weighted MSPmax.i of the group of bins are selected, and it is noted that these two values might not arise from the same bin. A Bradykinesia Score is produced by calculating:

$$BK = A \times \log 10(MSP\text{max} \times PKi) - B$$

This step thus operates upon the "best" or strongest movements in each 2-3 minute window. The BK score is then plotted against time.

BK11: A moving mean is taken of BK values over a 2 to 10 minute window (window length being a variable) and plotted against time, so as to filter the result for intuitive presentation to a neurologist.

The BK score produced by this algorithm thus enables a change in BK over time from each medication to be assessed, and the relative change in BK from the time of medication to be measured. This also allows an assessment of the percentage of time for which the patient is at each BK score for each day or each medication period. Noting that normally kinetic people can behave in a bradykinetic manner for short periods of time it is important to assess both the persistency and depth of the person's bradykinesia, which is made possible by this embodiment.

Dyskinesia Scoring Algorithm

The algorithm for producing an automated dyskinesia score stems from the recognition that dyskinetic subjects have few intervals or pauses between movement, while non-dyskinetic people will have longer periods of no movement. Dyskinetic persons will also move with a greater spectral power. This algorithm thus works to distinguish between normally kinetic people undergoing periods of excess voluntary movement and dyskinetic persons undergoing excess involuntary movement. The dyskinesia scoring algorithm operates on the recorded data in the following steps.

DK1: Band-pass filter the raw data to extract components in the range 1-4 Hz, in order to remove DC, wrist rotation, tremor and bumping of the sensor.

DK2: null

Steps DK3 to DK7 aim to remove sections of data that are above the mean acceleration, in an attempt to remove voluntary normal movements from the data set.

DK3: The data is broken down into 120 s bins which are each considered in isolation. The bin width is a variable, in this embodiment comprising 12000 data points. Longer bin periods are more likely to exclude movements of high acceleration because the majority of the signal will have smaller amplitude.

DK4 : For each 120 s bin i the mean acceleration amplitude ($Acc_i$) is measured, using the absolute amplitude of the data. $Acc_i$ is used as a threshold below which data is deemed to represent "reduced movement".

DK 5 : A one second (100 data point) moving point mean is calculated across the bin.

DK 6: Any one second duration of data for which the mean acceleration is larger than $Acc_i$ is removed from further consideration, in an attempt to exclude voluntary normal movements.

DK7 The remaining data in the bin is assumed to relate to periods of reduced movement and therefore is referred to as the reduced movement (RM) data set. The time period of the reduced movement within the bin is $T_{RM}$. The remaining RM data in the bin is simply concatenated.

Steps DK8-DK12 aim to measure the properties of the "non-voluntary" movement set remaining in the data, assessing several ways of measuring the power in the non-voluntary movements of the RM data. It is noted that dyskinetic patients have high power in their non-voluntary movements.

DK8A: a FFT is performed on the RM data set in each 120 s bin. The mean spectral power for the RM in each 120 s bin is the $SP_{RM}$. This is for the 1-4 Hz range due to the filtering at DK1. In dyskinesia this power will be higher than for normally kinetic persons.

DK8B: The RMS value of the Reduced Movement data set absolute values is taken, to give the reduced movement power.

DK8C: The variance (VAR) or standard deviation of the frequencies in either the full 120 s bin or in the RM data set is obtained.

DK9: A DK score is calculated as:

$$DKsp = A\, SP_{Rm}/T_{RM}$$

and DKsp is plotted.

DK10: A DK score is calculated as:

$$DKacc = \log_e(Acc_i \times SP_{RM})/T_{RM}$$

and DKacc is plotted.

DK11: A DK score is calculated as $$DKrms = A\, \log_e RMS_{RM}/T_{RM}$$

and DKrms is plotted.

DK12: A DK score is calculated as $$DKvar = A\, \log_e VAR/T_{RM}$$

and DKvar is plotted.

A moving mean is taken of DK values over a 2 to 10 minute window (window length being a variable) and plotted against time, so as to filter the result for intuitive presentation to a neurologist. Further, a percentage of time for which a patient is at different absolute DK scores for each day or each medication period is assessed. This recognises that a normally kinetic person can undergo dyskinetic-like movements for short periods, but that only dyskinetic patients have a relentless nature to their movements, which is what is measured in this approach.

This embodiment further provides for DK scores from a daily medication period, for example a 9:00 AM to 12:00 PM period, to be averaged over multiple days to obtain a stronger measure.

Figure 4:
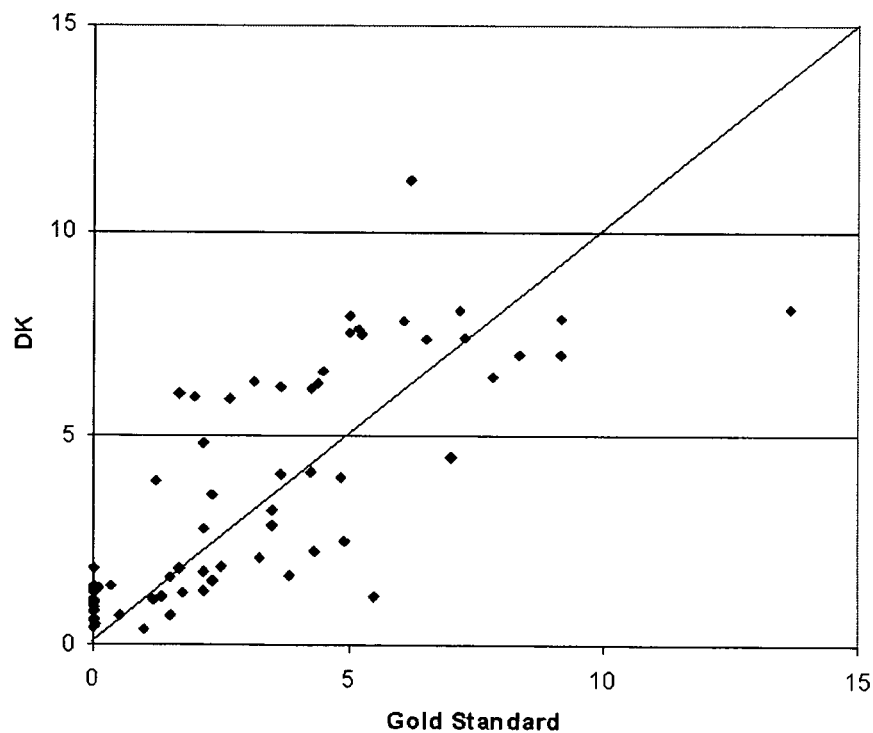
FIG. 4 is a plot of dyskinesia scores, with each point showing a score generated by one embodiment of the invention for a single dyskinetic episode plotted against the average of scores given by three neurologists observing the same episode.
Figure 5:
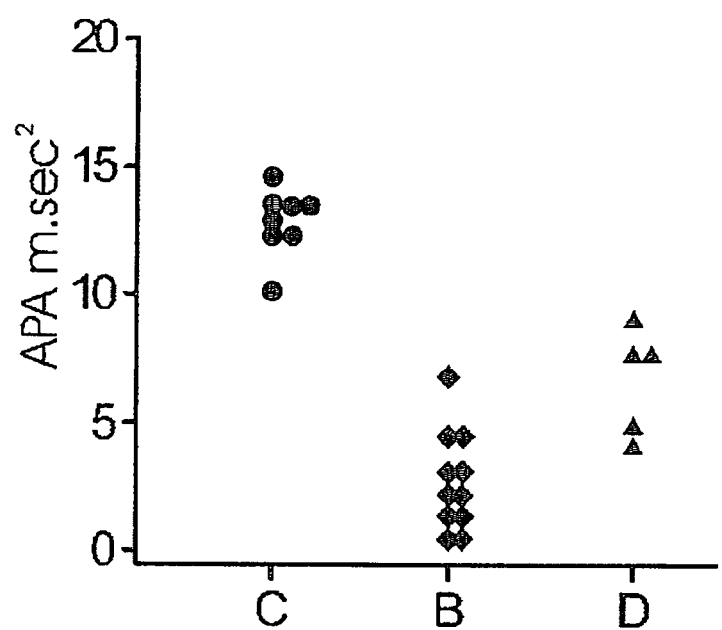
FIG. 5 illustrates the Average Peak Acceleration (APA) achieved during task 2 bradykinesia score) plotted for each subject group (C=Controls, B=bradykinetic and D=dyskinetic subjects)

FIG. 4 is a plot of dyskinesia scores, with each point showing a DK score generated by one embodiment of the invention for a single dyskinetic episode plotted against the average scores of dyskinesia given by three neurologists observing the same event. As can be seen the present invention compares favourably with the average score of three neurologists (referred to as the "Gold standard"), (specificity 93.6%; sensitivity 84.6%), demonstrating that this embodiment is an acceptable replacement for daily clinical monitoring.

Figure 11:
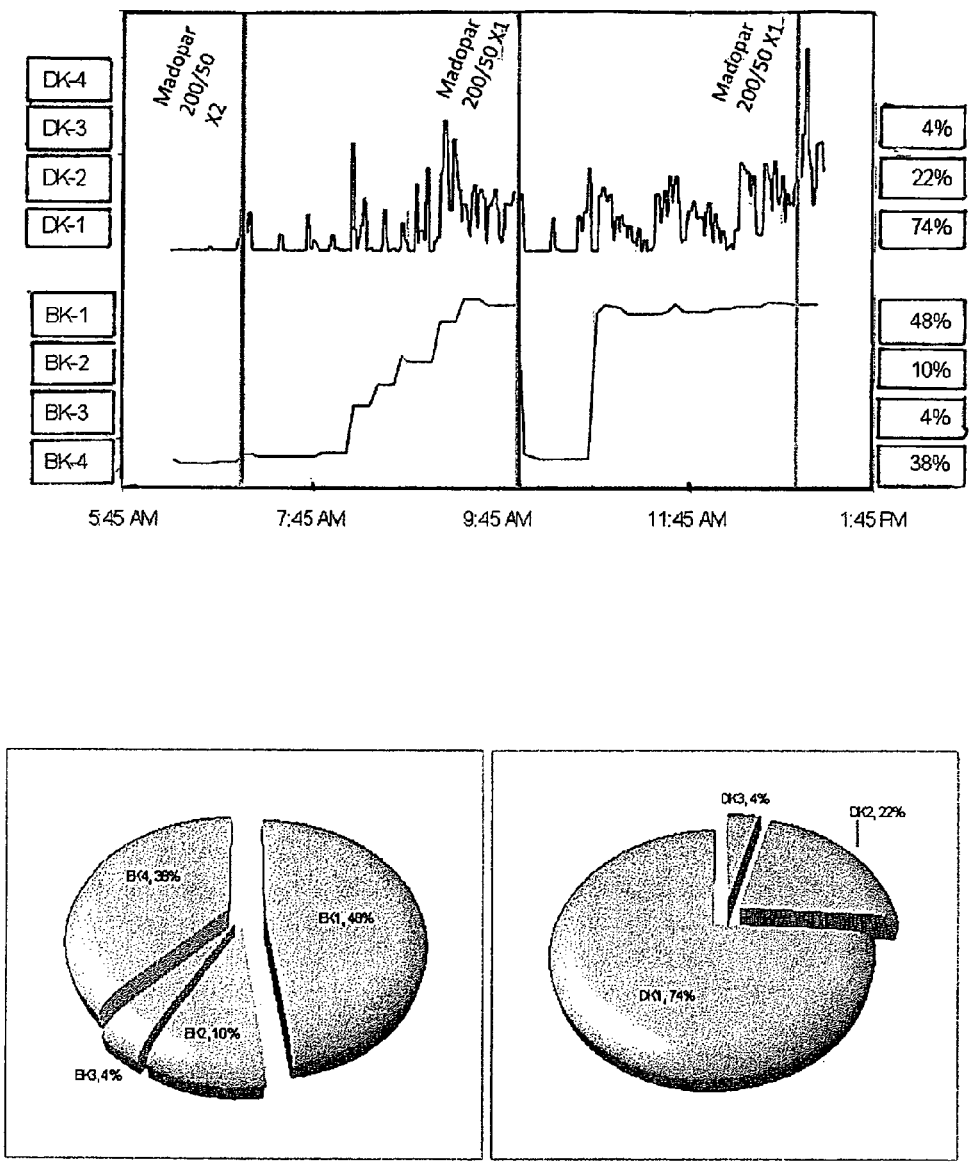
FIG. 11 is a resulting scan of the patient and resultant determination using the apparatus and system of the invention.

FIG. 11 illustrates results obtained using the system of FIG. 2 and using the above algorithms, for one patient. The patient woke at 6:15 am and put the wrist recording device on. Her movements caused the device and algorithm to give a very low BK score of BK4 at this time, which shows her to be very bradykinetic which is the principle feature of Parkinson's disease. She then took two tablets of L-Dopa at 7:00 am but remained bradykinetic until the tablets were absorbed and there was enough concentration in the brain to start to reduce her bradykinesia. From about 8:00 am until 9:30 am her bradykinesia continued to improve from BK4 up to BK1, BK1 being normal pattern movement. However, the concentration of L-Dopa at this stage also started to introduce peak dose dyskinesia at about 9:00 am. She relapsed into BK state near 10:00 am. Her second medication was taken at 10:45 am which soon returned her to a normal BK score of BK1. Dyskinesia developed again around 12:30 pm.

As will be appreciated such a simultaneous, ongoing and objective measure of both bradykinesia and dyskinesia provides a neurologist with detailed information to assist in formulating a suitable regime of medication. For example, in response to this recording a neurologist may elect to move the first dose of L-Dopa to earlier in the morning to reduce her bradykinesia time, then make the time interval to the second dose somewhat shorter while maintaining the interval to the third dose. The aim for this patient would be to maintain BK for a higher percentage of time in the BK1 state, while also aiming to reduce the DK score so that less time is spent in DK2 and DK3 states. Naturally, further measurements can be taken in accordance with the present invention to monitor the effect of such a change.

This embodiment thus provides for the bradykinetic and dyskinetic states of the person to be recognised and quantified with high selectivity and sensitivity, even when the person is carrying out normal daily activities across a range of naturalistic movements and not controlled movements in a clinical environment.

Figure 14:
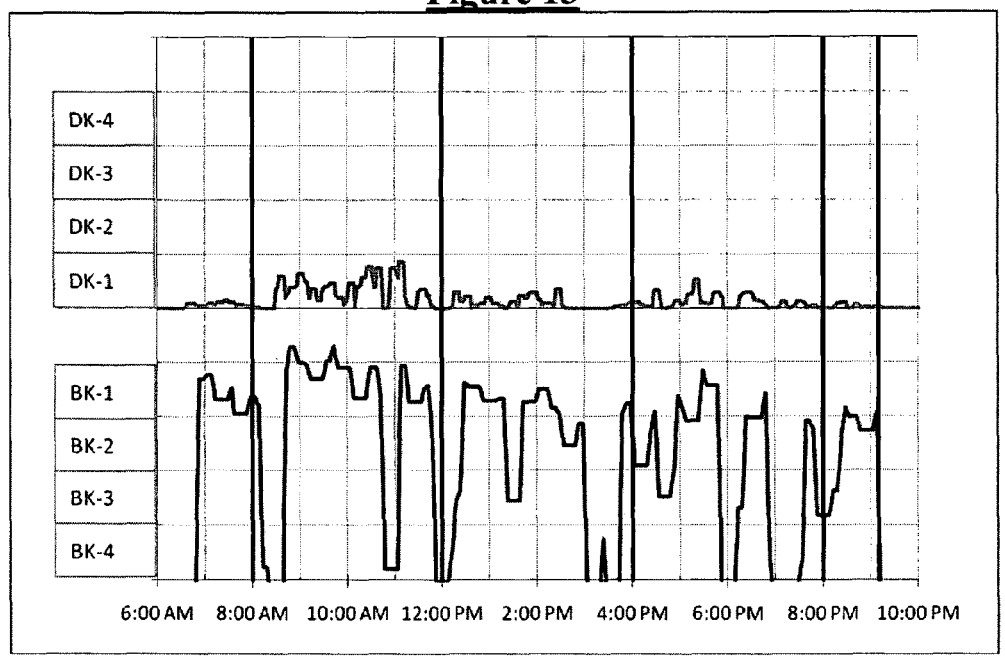
FIG. 14 is a graph illustrating substantially continuous DK and BK scoring for an individual throughout the course of a day.

FIG. 14 illustrates substantially continuous DK and BK scoring for an individual throughout the course of a day. L-dopa treatments were taken at the times indicated by the vertical lines. This figure produced by the present embodiment of the invention clearly indicates that the patient has very low dyskinesia and very significant bradykinesia, enabling a neurologist to quickly deduce that the patient appears to be undertreated.

Figure 15:
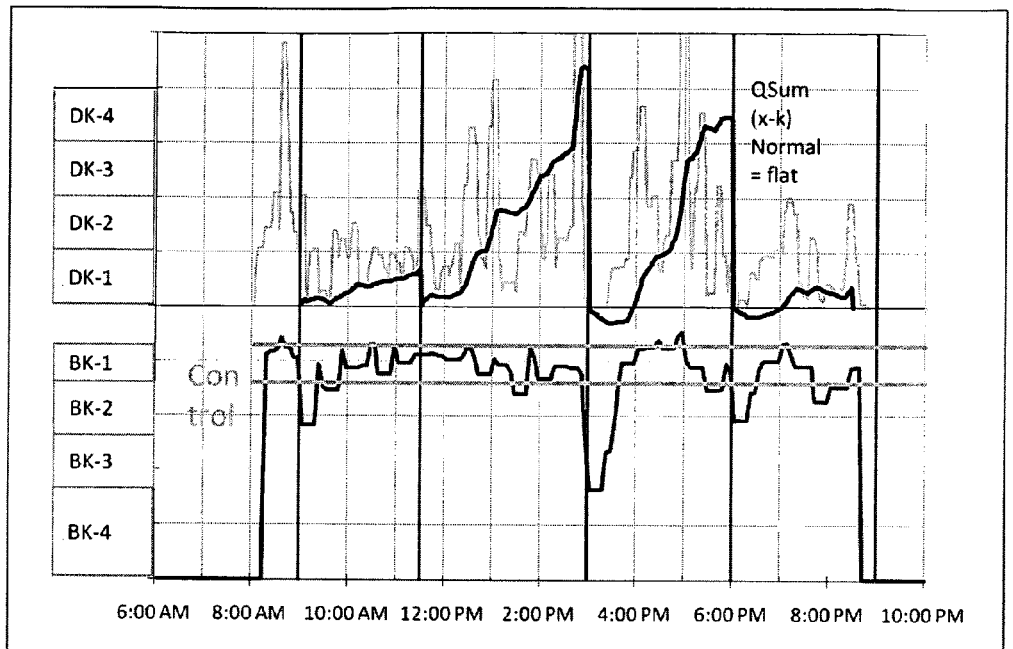
FIG. 15 is a graph illustrating an alternative manner in which the results of the invention may be presented, by plotting a cumulative sum of DK scores for the period following each dose together with the value of BK scores throughout the day.

FIG. 15 illustrates an alternative manner in which the results of the present technique may be presented, by plotting a cumulative sum of DK scores for the period following each dose. The actual DK scores are shown in faint lines with the cumulative DK score (CUSUM DK) indicated by the solid line. Again, the time of each medication is indicated by a vertical line. A flat CUSUM indicates a normal kinetic state, and so FIG. 15 illustrates that this patient experiences significant dyskinesia, particularly during the afternoon. In this case the present invention thus provides the neurologist with valuable information regarding the dyskinesia induced by each particular dose throughout the course of the day. FIG. 15 also plots the value of BK scores throughout the day.

Figure 16:
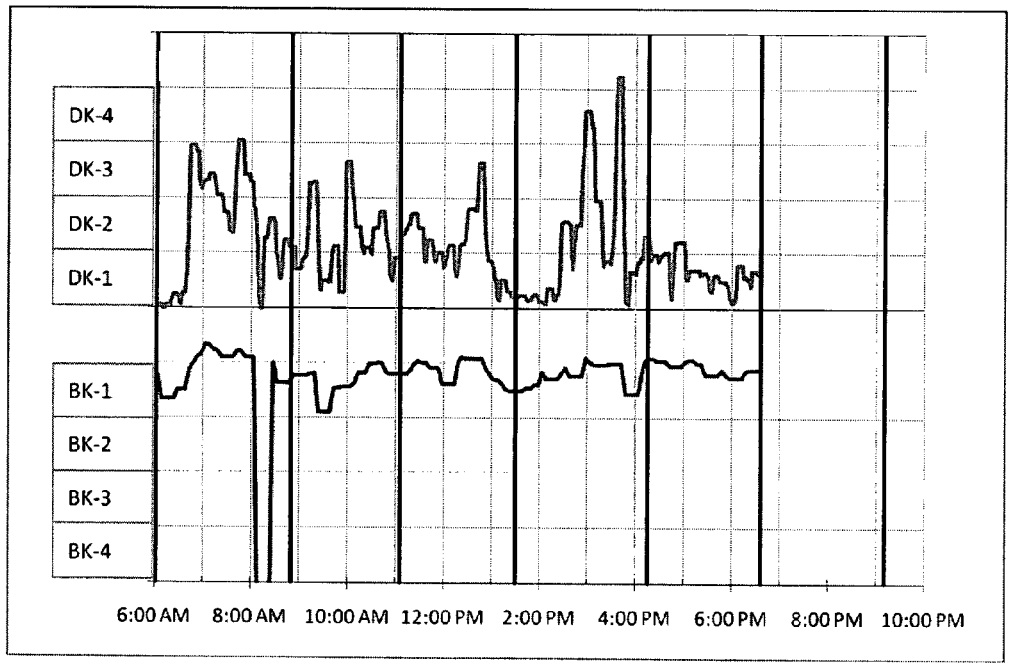
FIG. 16 is a graph which plots DK and BK scores for a patient who is dyskinetic.

FIG. 16 plots DK and BK scores for another patient, who can be seen from these results to be very dyskinetic. This patient's BK scores are largely normal thus providing a neurologist with valuable insight that medication might be lowered as bradykinesia has been fully treated but high dyskinesia is occurring. The aberrant BK scores around 8:15 AM might have been caused by the patient removing the logger for example when taking a shower.

On testing a form of the device and system on test subjects the following occurred: Twelve subjects, patients with Parkinson's Disease, and eight healthy subjects (controls) were studied (Table 1). Subjects were recognised as being bradykinetic [B], dyskinetic [D] and normal [C]. The Parkinson's Disease patients were drawn from one clinic and were receiving medication for Parkinson's Disease. The controls had no known neurological disorders. All procedures complied with the World Medical Association Declaration of Helsinki and were approved and supervised by a Human Research & Ethics Committee. All subjects provided consent following a detailed explanation of the experimental procedure.

TABLE 1

| Subjects | |
|---|---|
| Normal Subjects (C) | 8 (4 F) Average age, 48 ± 13 |
| Parkinson Subjects | 11 (7 F) Average age, 67 ± 86 |
| Bradykinetic (without tremor, B) | 6 |
| Dyskinetic (D) | 5 |
| Disease duration | 9 ± 4 |
| Age at disease onset | 58 ± 10 |

Treatment of L-Dopa

To ensure that the patients were bradykinetic at time zero, they were requested to withhold their regular therapy 10 hours prior to commencement of the study. Food and fluid intake was not restricted. A single tablet of 250 mg of L-dopa and 25 mg of carbidopa was given to the patients at the beginning of the study (0 minutes). The patients were then requested to complete a set of simple tasks administered at 0, 10, 20, 30, 45, 60, 90, 120, and 180 minutes after drug administration.

Clinical Assessment.

Bradykinesia was assessed by measuring maximum acceleration while performing a repetitive, oscillatory movement. Subjects were asked to slide their forefinger between two large dots (diameter 30 mm) placed 300 mm apart on a piece of cardboard. This was performed for 30 seconds at their own pace, followed by a 30 second rest and then repeated as fast as possible for 30 seconds. The dots were positioned so that the limb movement was across the body rather than to and from the body. This was a variation on the well known and validated key press or peg board tests for assessing bradykinesia. The averaged peak acceleration (APA) was the median of the 20 greatest accelerations and was used as the clinical bradykinesia score.

A dyskinesia score was obtained from the average of scores provided by trained neurologists familiar with Parkinson's disease and experienced in the use of the modified IMS scoring method. Two of the evaluators had not previously examined any of the patients used in this study; the third evaluator provided their routine neurological care. The evaluators scored independently of their colleagues.

Subjects were videoed while they performed 5 specified tasks (described later). The video was divided into 30 s epochs and the evaluators provided a score for each epoch. A Modified Involuntary Movement Score (IMS), modified from previously described methods was used to provide a score of 0-4 for each of the following five body regions: Upper extremities; arms, wrists, hands and fingers, Lower extremities; legs, knees, ankles and toes, Trunk movements; back, shoulders and hips: Head movements; neck and facial: Global Judgments; overall severity of dyskinesias. The scores were as follows: 0=no dyskinesia present: 1=dyskinesias discernable to a trained physician, except not a layperson: 2=dyskinesias easily detectable: 3=dyskinesias that would affect day-to-day activities but do not restrict them: 4=dyskinesias that would restrict day-to-day activities. Thus the maximum IMS was 20.

Test Procedures

The accelerometer was oriented so that it was most sensitive to pronation/supination movements and was attached to the most severely affected limb of Parkinsonian subjects and on the dominant limb of control subjects. The lead of the accelerometer was secured separately below the elbow, so as to prevent adventitial movement of the accelerometer. Subjects then performed the following tasks.

Task 1. Unrestricted voluntary movement: Subjects were engaged in conversation about a subject that required descriptions of how to make, build or do something, such as tying a neck tie. Spontaneous movements were recorded to establish whether bradykinesia and dyskinesia could be detected using the spectrogram, during normal activities and not only during specially selected tasks.

Task 2. Voluntary repetitive alternating movements: This was described previously (clinical assessment) and was used to obtain a clinical bradykinesia score.

Task 3. Restricted voluntary movement: Subjects were requested to remain as still as possible in an attempt to identify involuntary movement, such as dyskinesia. The subjects were instructed to sit upright with their hands on their knees and were requested to refrain from voluntary movement for 1 minute. Subjects were scored for dyskinesia during this task.

Task 4. Patients poured water from a 1 L jug, filled to 600 ml, into three plastic 250 ml cups. This task took between half a minute to two minutes to perform. Patients were asked to pour using the wrist with the accelerometer attached.

Task 5. The patients walked a distance of 2.5 meters turned 180° and walked a further 2.5 meters. This was repeated for at least 30 s although some subjects took a minute to perform one cycle. One patient was confined to a wheelchair and was unable to perform this task.

Each task took approximately 2 minutes to perform. In the first part of the study, the subjects completed the first three tasks once. Following the test dose of L-dopa, subjects were requested to perform all five tasks at regular intervals after drug administration. This trial was designed to encompass the effects of a single dose of L-dopa and include the consequent short-term motor fluctuations.

Statistical Analysis

Figure 7:
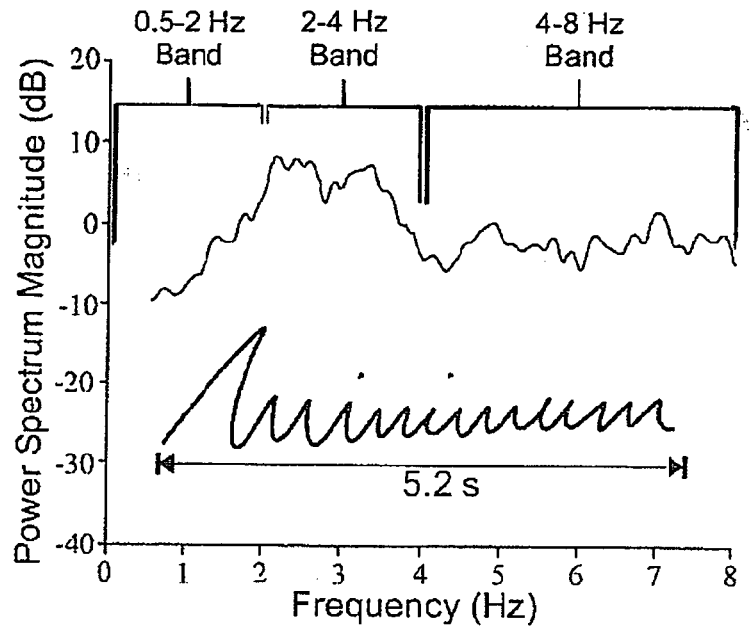
FIG. 7 illustrates the power spectrum obtained from a normal subject while writing the word "minimum"

The 0.5-8.0 Hz frequency band was divided into three bins or bands of frequency: 0.5-2.0 Hz, 2.0-4.0 Hz, and 4.0-8.0 Hz (FIG. 7). The frequency bands were selected to represent frequencies that may be relevant to specific movement behaviours. As the FFT is a line drawn through a series of discrete points, all the points in a band could be summed and averaged to produce a mean that will be subsequently referred as the MSP (mean spectral power) for the frequency band. Thus $MSP^{0.5-2.0\ Hz}$ will refer to the mean spectral power from the frequency band of 0.5 to 2.0 Hz.

In the first stage of the study a comparison was made between the MSP obtained from the bradykinetic and the dyskinetic subjects using the Mann-Whitney test and a P value less than 0.01 was considered significant. Even though tests for statistical significance were performed, the only functionally useful result would be to achieve little or no overlap between various clinical groups for a particular test.

Results

Selection and Characterisation of Bradykinesia and Dyskinesia in Subjects with Parkinson's Disease.

Patients in this study were selected because they had either obvious bradykinesia (known as bradykinetic patients) or prominent dyskinesia following a dose of L-dopa (dyskinetic subjects). Bradykinetic subjects were assessed when off medication but most did not develop prominent dyskinesia when on L-dopa. We used the APA (described in the methods) from the dot slide, as the 'standard' for bradykinesia severity. The APA scores of dyskinetic subjects was intermediate between normal and bradykinetic. A total IMS score was provided by three neurologists who gave a dyskinesia score for each two minute segment of videoed movement. Agreement between the three evaluators was reflected in the strong correlations between their scores

TABLE 2

Spearman Rank order correlations between the different evaluators' scores of dyskinesia.

|  | Elevator 2 | Elevator 3 |
| --- | --- | --- |
| Elevator 1 | r = 0.796 | r = 0.860 |
| Elevator 2 |  | R = 0.915 |

All r values were significant (p < 0.01)

Importantly, the IMS score for the recorded arm correlated highly (r=0.85, see also FIG. 13) with the total IMS score justifying the measurement of acceleration in a just one arm (FIG. 13).

Figure 6A:
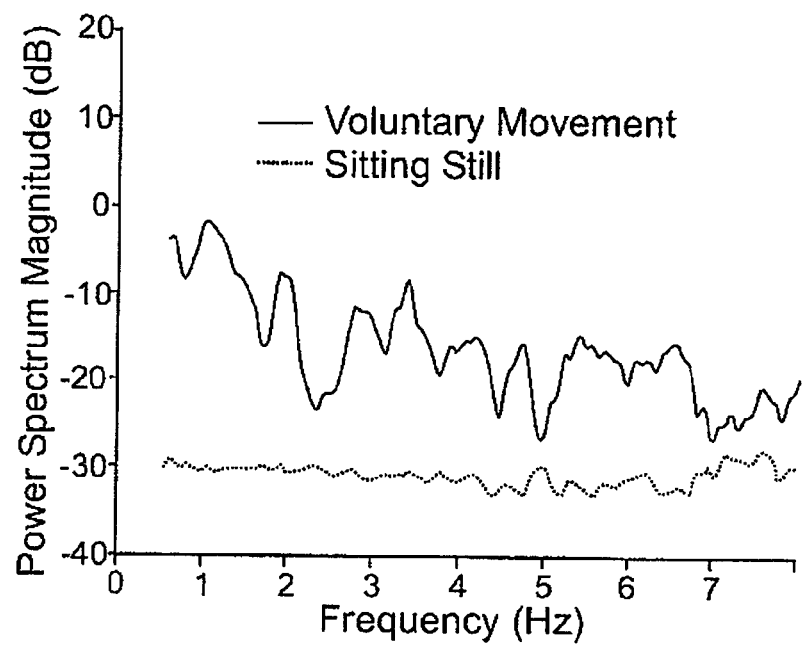
FIG. 6A illustrates the power spectrum obtained from a normal subject while sitting still (dotted line, task 3) and while performing voluntary movements (task1, heavy line)
Figure 6B:
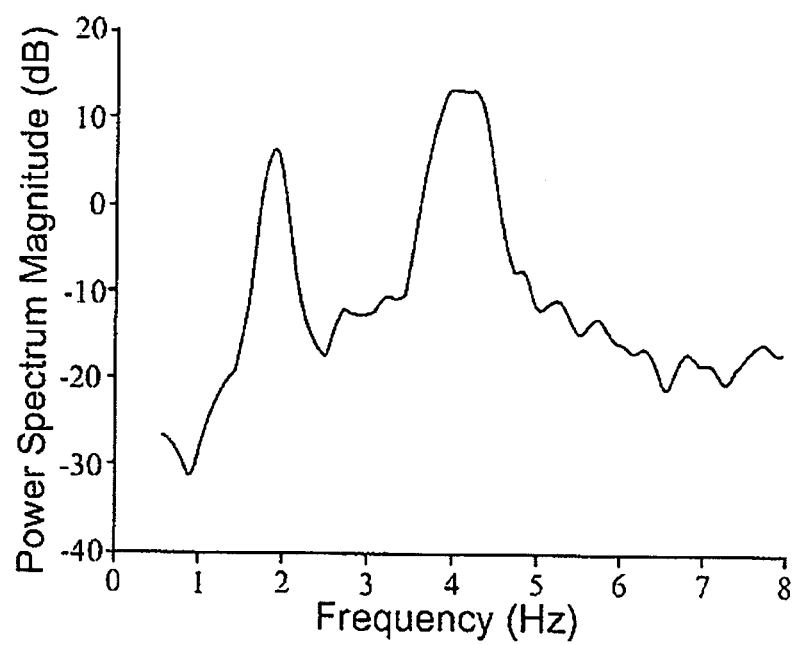
FIG. 6B illustrates the spectral output when the subject was asked to use the fore finger to track 2 Hz and 4 Hz oscillations moving across the face of an oscilloscope.

The next set of studies addressed the question of whether the Power spectrum of normal subjects was suitable for identifying different movements. When a normal subject was sitting still (task 3, FIG. 6A), the power across the broad range of studied frequencies was lower than when the subject was engaged in voluntary movement (task 1, FIG. 6A). To then demonstrate that 2 and 4 Hz limb oscillations could be measured, normal subjects used their fore finger to track 2 and 4 Hz oscillations on an oscilloscope screen. Clear peaks at the relevant frequencies were apparent in the power spectrum (FIG. 6B). When subjects wrote the word "minimum", a broad peak at approximately 3 Hz was apparent (FIG. 7).

Figure 8:
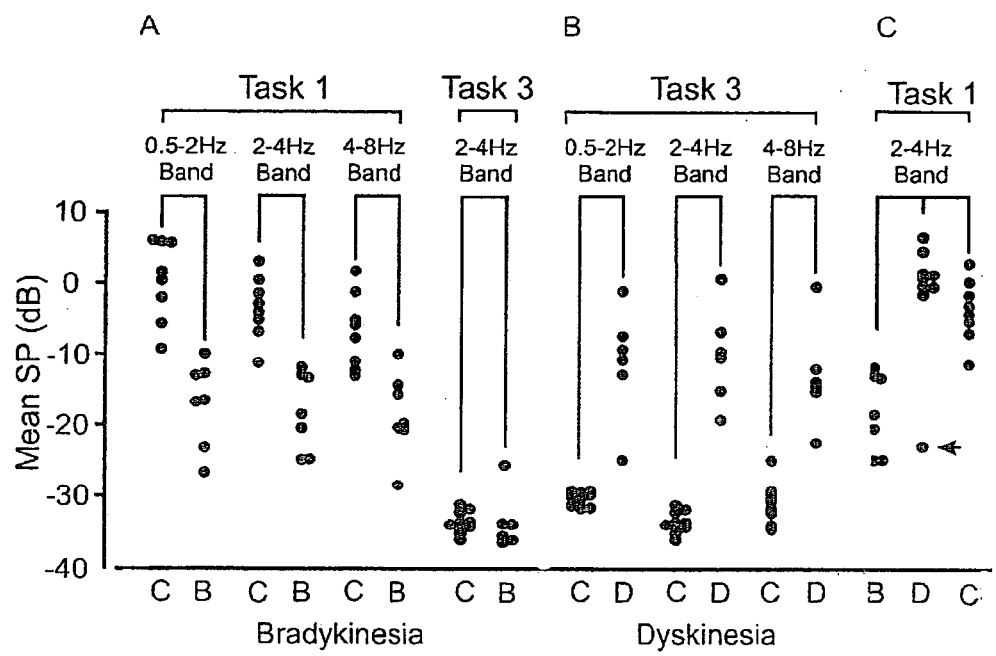
FIG. 8 is a plot of the MSP for normal (C), bradykinetic (B) and dyskinetic (D) subjects for each spectral band and performing Task 1 or Task 3.

The Power Spectrum was then divided into three bands (FIG. 7) and the MSP of each band was estimated (FIG. 8). When moving the wrist during conversation (task 1), power spectrum in all three frequency bands was lower in bradykinetic subjects than in normal subjects (FIG. 8). Not surprisingly this difference was less apparent when subjects were asked to remain still: bradykinetic patients could keep as still as normal subjects (e.g. task 3, FIG. 8).

The frequency range of dyskinetic movements was similar to normal movements but with a substantially increased power. As might be expected, dyskinetic subjects had difficulty remaining completely still (task 3 FIG. 8). Although the MSP of normal and dyskinetic subjects was completely separated in each of the three spectral bands, the separation was greatest in the $MSP^{2.0-4.0\ Hz}$ (task 3 FIG. 8).

Bradykinesia

The $MSP^{2.0-4.0\ Hz}$, from all patients at all time points were correlated with the APA measured at the same time point

TABLE 3

Pearson correlations (n = 79 for all Tasks) between the $MSP^{2.0-4.0\ Hz}$ and APA.

| Task 1 | Task 3 | Task 4 | Task 5 |
|---|---|---|---|
| Talking Freely | Sitting Still A | Pouring Water | Walking |
| 0.320* | r = 0.146 | r = 0.400* | r = 0.264 |

*= significant r values (p < 0.01)

$MSP^{2.0-4.0\ Hz}$ correlated poorly with bradykinesia (as measured by the APA). This was reflected in a low specificity (76%) and sensitivity (65.1%) of the $MSP^{2.0-4.0}$ Hz to predict bradykinesia.

The poor correlations most likely arise because bradykinesia measured by MSP was task dependent. For example, when a normal person "chose" to sit still, the MSP would be indistinguishable from a bradykinetic, who does not have the capacity to move faster. Thus, the requirement was to recognise patients who were still for much of the time but capable of making rapid movements from bradykinetic patients who were not capable of fast movements. On consideration, bradykinetic subjects make fewer movements than normal subjects and hence there are longer intervals between movements. Furthermore, when bradykinetics movement occurs, the movements are of lower power, reflecting lower acceleration and amplitude.

Figure 9A:
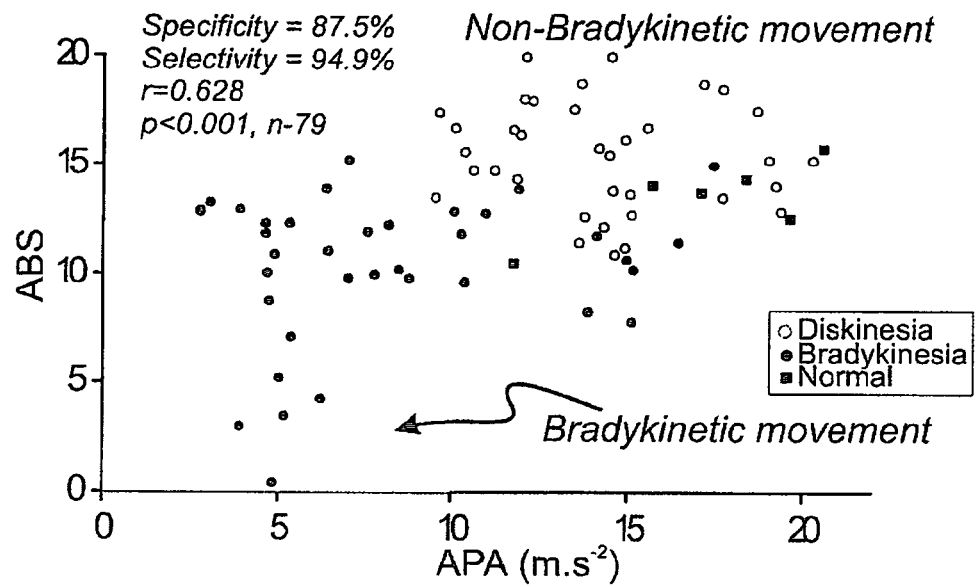
FIG. 9A is a plot of APA against the ABS.
Figure 9B:
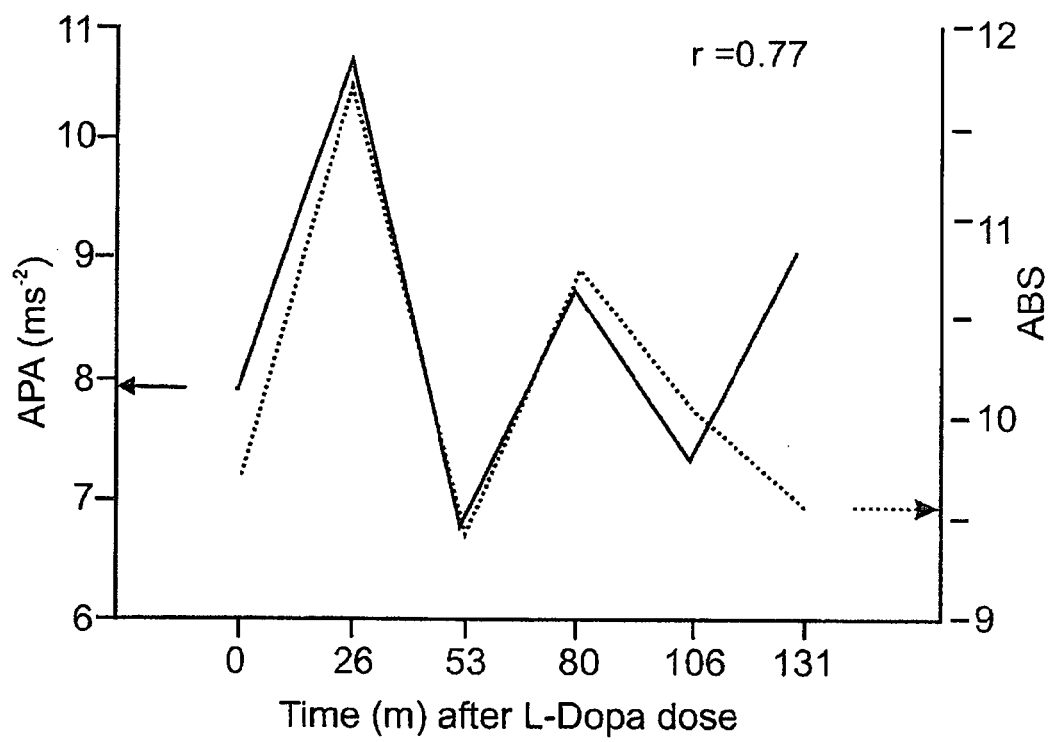
FIG. 9B illustrates changes in bradykinesia of a single patient plotted against time after a dose of L-dopa, with the heavy line being bradykinesia as determined by the APA and the dotted line being bradykinesia as determined by the ABS.

An algorithm in accordance with one embodiment of the present invention was thus developed which, in essence, used the maximum acceleration made in each interval and the MSP in the period surrounding this peak to produce an ABS (automated bradykinesia score). The argument was that normal subjects may have periods of low MSP but whatever movements they do make would be done with much higher acceleration than bradykinetic subjects. The algorithm used to derive the ABS was modified serially and optimised against the APA. When optimal, a new set of data was collected and plotted against the APA (FIG. 9A). The ABS strongly correlated with the bradykinesia "standard" (r=0.628, p<0.001, n=79) with a specificity of 87.5% sensitivity of 94.5%. The APA and the ABS were plotted against time after a dose of L-Dopa and the example of one subject is shown in FIG. 9B. In this case the correlation between APA and ABS was r=0.77.

Dyskinesia

An Automated Dyskinesia Score (ADS) was also developed. The Clinical Dyskinesia Score was found to be strongly correlated with both the $MSP^{1-4\ Hz}$ and the APA

TABLE 4

Pearson's correlations between the $MSP^{2.0-4.0\ Hz}$, the APA and the Clinical Dyskinesia Score.

|  | APA | Clinical Dyskinesia Score |
|---|---|---|
| MSP | r = 0.90 | r = 0.89 |
| APA |  | r = 0.85 |

All r values were significant (p < 0.01).

In view of these correlations, either accelerometer measure would provide an objective measure of dyskinesia that would concur with neurological assessment. However, the sensitivity (76.9%) and specificity (63.6%) of the MSP was unacceptably low. The correlation was highly dependent on the task being performed by the patient. In particular, this correlation did not take into account dyskinesia when the subject was sitting still, and the level of dyskinesia was markedly higher when the subject was walking even though it occurred only 30 seconds later. Thus the problems with Spectral power as a measure of dyskinesia were similar to those encountered with bradykinesia: namely, the problem of distinguishing between periods of increased voluntary movement and increased involuntary movement (dyskinesia). Examination of dyskinetic subjects and discussion with neurologists suggested that dyskinetic subjects would have shorter time periods without movement.

Figure 10A:
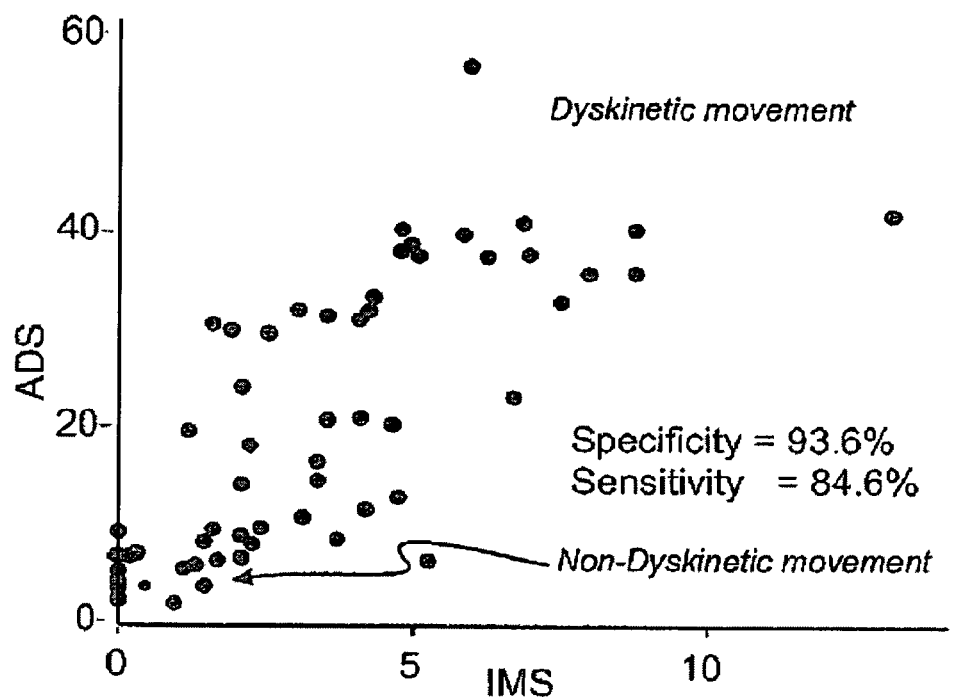
FIG. 10A illustrates the IMS plotted against the ADS.
Figure 10B:
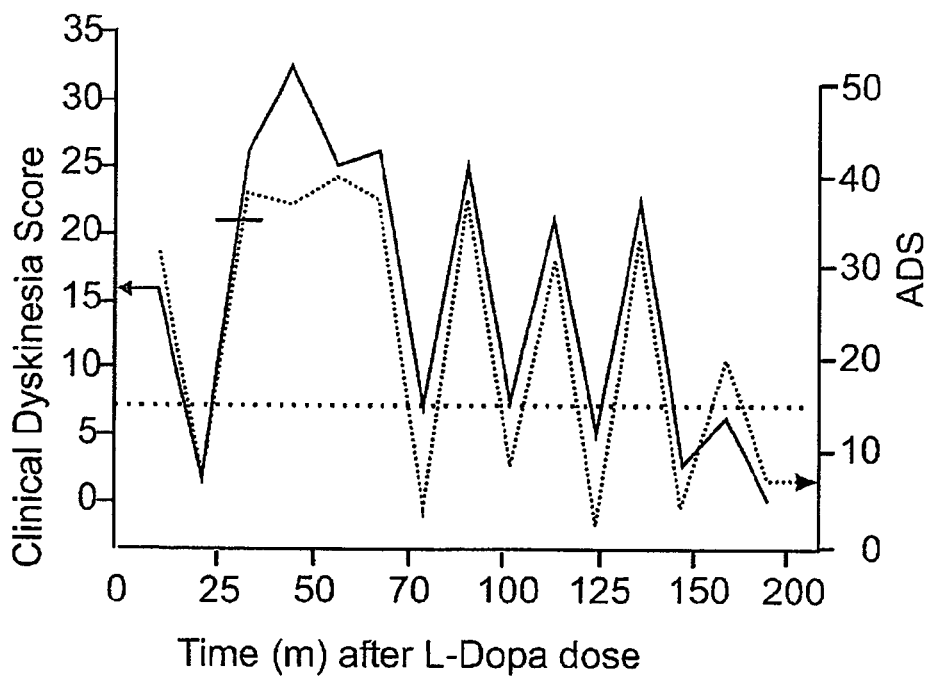
FIG. 10B illustrates changes in dyskinesia of a single patient plotted against time after a dose of L-dopa, with the heavy line being dyskinesia as determined by the APA and the dotted line being dyskinesia as determined by the ADS.

Thus, in accordance with one embodiment of the invention, a DK algorithm was developed to identify periods where movement was absent or of low amplitude in the accelerometer recording. In brief, the mean acceleration in each 2 minute segment was estimated and movements above average acceleration were regarded as either voluntary or dyskinetic movements. Epochs where acceleration was less than the mean were extracted and the $MSP^{1.0-4.0\ Hz}$ was divided by the number of low acceleration epochs to provide an Automated Dyskinesia Score (ADS). Non-dyskinetic subjects should have greater periods below the mean acceleration and a lower $MSP^{1.0-4.0\ Hz}$, Dyskinetic subjects on the other hand should have less time below the mean acceleration window, and should have a large $MSP^{1.0-4.0\ Hz}$. In essence the approach is to quantify the duration of time that the subject remains still. The algorithm of this embodiment used to derive the ADS was modified serially and optimised against the IMS. When optimal, a new set of data was collected and plotted against the IMS and a correlation co-efficient (Spearman's) was calculated (r=0.766, p<0.0001, n=85, FIG. 10A). While this correlation was less than that between $MSP^{1-4\ Hz}$ and the IMS, the sensitivity and specificity was much higher (sensitivity=84.6%, specificity=93.6%). The method was better suited for long-term recording of patients, because it was less influenced by the type of task performed.

An assumption underlying these embodiments of the invention was that patterns of movement recognised by a trained observer can be quantified by recording a trace of the movement and modelling the features that the observer uses to characterise the pattern. In this study we first showed that spectral analyses could distinguish between bradykinesia and dyskinesia. However the sensitivity and selectivity of this method degraded when a variety of activities occurred.

In particular more complex analysis was required to distinguish between bradykinesia and a normal subject sitting still, and between dyskinesia and some forms of normal activity. This was achieved by modelling what trained observers see: bradykinetic subjects have longer intervals between movement and when they do move it is with lower acceleration. Dyskinetic subjects have fewer intervals between movement and they move with a greater spectral power. Using this approach it was possible to recognise bradykinetic and dyskinetic movements with high selectivity and sensitivity across a range of naturalistic movements.

To verify this embodiment of the invention involved reference to a "gold standard". Clinicians know dyskinesia and bradykinesia when they see it and clinical scales have been developed in an attempt to quantify clinical observation. However these scales are subjective, require training and experience and are most precise when repeated by the same clinician. Of necessity these scales can only be used when a trained observer is present, but Parkinson's Disease varies greatly over the day, from day to day and one single snap shot cannot provide a true measure of function or fluctuation in disease. The bradykinesia and dyskinesia rating scales used are the most widely accepted semi-objective methods available to compare with the output of spectral analyses. The most common clinical bedside test for bradykinesia is to request rapid alternating finger movements. Slow small amplitude movements (low acceleration) are considered bradykinetic and there are several quantitative scales that measure peak acceleration developed during oscillatory movement such as peg board, key press and dot-slide (task 2). These vary according to the number of repetitions or, timing of movement or "amount" of movement achieved. Similarly, low amplitude slow handwriting and key presses per minute are well-validated tests for bradykinesia. Each of these scales depends on the inability to reach normal acceleration as a measure of bradykinesia. The dyskinesia score was a modification of other dyskinesia rating scales. The degree of correlation between the clinical scales and the automated scales of the present embodiment suggest that the automated scales are of value and could be used to continually score the clinical state over a protracted period. The DK and BK scores are capable of recognising the clinical states and may thus provide an effective clinical tool.

Thus, the described embodiment of the invention recognises that improved management of PD by medication requires monitoring of both bradykinesia and dyskinesia, even when away from clinical observation, throughout the day. The present embodiment thus provides a means to remotely and substantially continuously capture, interpret and report a patient's movement status over a defined period of time. Because this system reports automatically to the neurologist, there is no need for the patient or their carer to worry about remembering, keeping or maintaining records. Further, the simple wrist-worn device of this embodiment is easy to use and can be used at home or elsewhere and does not intrude on day to day activities, being a simple system that does not require an understanding of technology. Further, for people living in rural and remote areas who are unable to easily attend clinics in major centres, changes to dosage can be made by the neurologist remotely, in conjunction with the patient's local GP.

The presently described embodiment of the invention is further beneficial to the neurologist by automatically providing the neurologist with an objective assessment (in digital report format) of the symptoms experienced by patients with Parkinson's Disease (PD). This provides neurologists with reliable information about a patient's kinetic status over a meaningful period, based on objective and continuous data capture. With this information, physicians can titrate medication more efficiently to reduce the incidence of dyskinesia and bradykinesia, key symptoms for PD sufferers. This results in improved patient management and a better quality of life for people living with PD. This may further result in fewer visits to doctors/clinics, allowing a neurologist to provide effective care to a greater number of patients.

Wider benefits of this embodiment may include improved patient management that decreases the financial burden on health care systems, fewer day patient visits, reduced incidence of symptom-associated falls and complications requiring hospitalization, and reduced high and specialised aged care.

This embodiment further provides for the wrist-worn device to be programmable whereby the neurologist can set the time and frequency for recording, based on the needs of the patient, and can further cause the device to give reminders to the patient for taking medication.

This embodiment thus provides an objective reporting tool that remotely records PD patients' movements on a continuous basis and provides an assessment every 2-3 minutes, for the number of days required by the neurologist. It solves the problem of reliable measurement of PD symptoms and automatically provides reports to the neurologist via email or a suitable website. While helpful for all PD stages, it is particularly valuable during the middle stages of the disease, when dyskinesia begins to emerge. Physicians can diagnose disease progression and change medication dosage based on objective data recorded for 3-4 days before a patient's visit. They can determine dosage effectiveness or make further changes using data recorded after dosage is altered. Records are easy to retain with the patient's history.

The present embodiment thus provides an objective continuous assessment of the symptoms experienced by patients with Parkinson's disease. This embodiment may thus assist physicians to more inefficiently determine instances of bradykinesia and dyskinesia and therefore improve patient management by providing better medication, giving improved quality of life for people with bradykinesia and/or dyskinesia, such as persons having Parkinson's disease.

Some portions of this detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

As such, it will be understood that such acts and operations, which are at times referred to as being computer-executed, include the manipulation by the processing unit of the computer of electrical signals representing data in a structured form. This manipulation transforms the data or maintains it at locations in the memory system of the computer, which reconfigures or otherwise alters the operation of the computer in a manner well understood by those skilled in the art. The data structures where data is maintained are physical locations of the memory that have particular properties defined by the format of the data. However, while the invention is described in the foregoing context, it is not meant to be limiting as those of skill in the art will appreciate that various of the acts and operations described may also be implemented in hardware.

It should be borne in mind, however, that all of these and similar terms are to be associated with the appropriate physical quantities and are merely convenient labels applied to these quantities. Unless specifically stated otherwise as apparent from the description, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description; In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Figure 12:
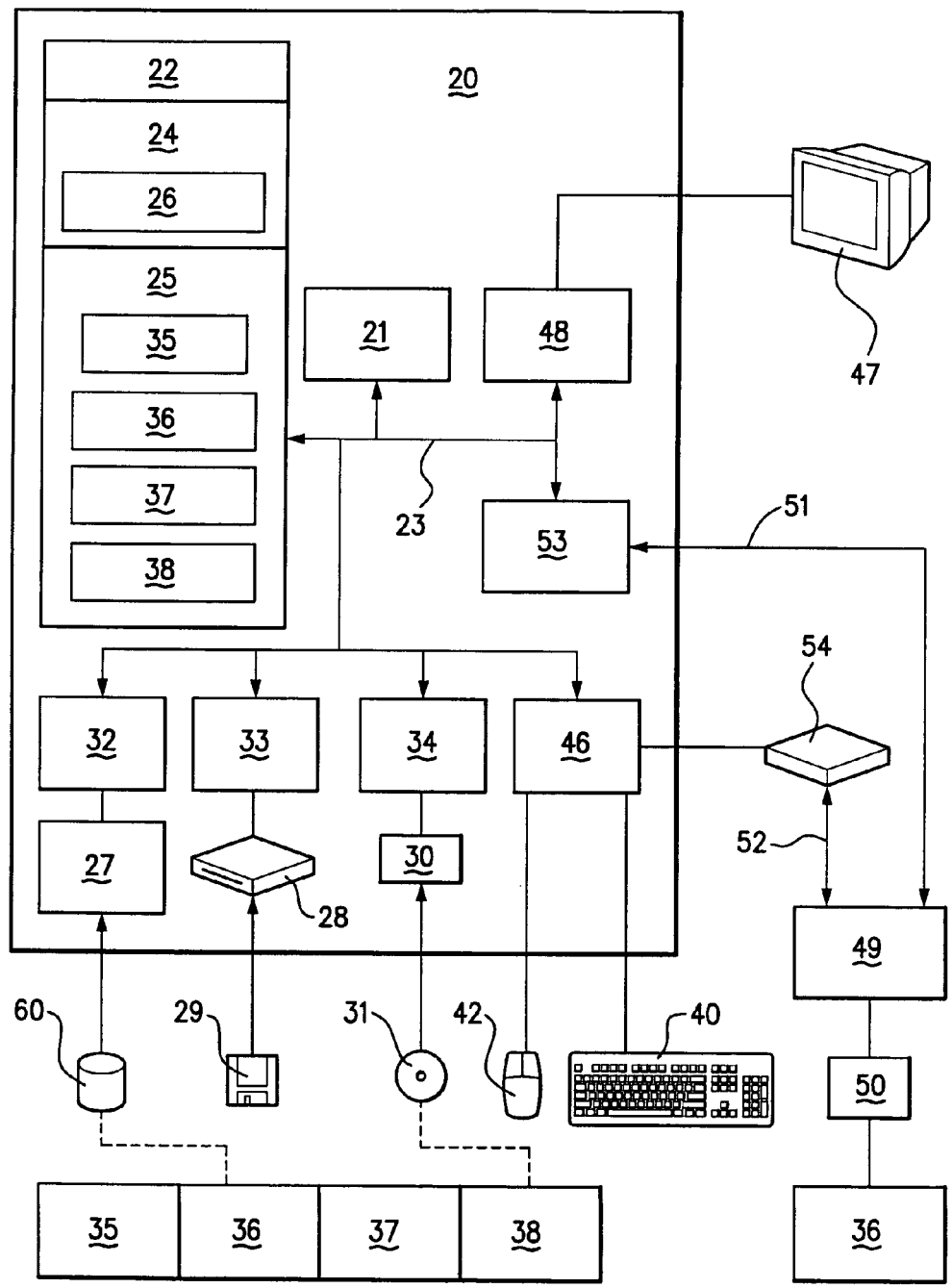
FIG. 12 illustrates a general-purpose computing device that may be used in an exemplary system for implementing the invention.

Turning to FIG. 12, the invention is illustrated as being implemented in a suitable computing environment. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multi-processor systems, microprocessor-based or programmable consumer electronics, network PCs, minicomputers, mainframe computers, and the like. The invention may be practiced in distributed computing environments where tasks are performed by remote processing devices that are linked through a communications network. In a distributed computing environment, program modules may be located in both local and remote memory storage devices.

In FIG. 12 a general purpose computing device is shown in the form of a conventional personal computer 20, including a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help to transfer information between elements within the personal computer 20, such as during start-up, is stored in ROM 24. The personal computer 20 further includes a hard disk drive 27 for reading from and writing to a hard disk 60, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer readable instructions, data structures, program modules and other data for the personal computer 20. Although the exemplary environment shown employs a hard disk 60, a removable magnetic disk 29, and a removable optical disk 31, it will be appreciated by those skilled in the art that other types of computer readable media which can store data that is accessible by a computer, such as magnetic cassettes, flash memory cards, digital video disks, Bernoulli cartridges, random access memories, read only memories, storage area networks, and the like may also be used in the exemplary operating environment.

A number of program modules may be stored on the hard disk 60, magnetic disk 29, optical disk 31, ROM 24 or RAM 25, including an operating system 35, one or more applications programs 36, other program modules 37, and program data 38. A user may enter commands and information into the personal computer 20 through input devices such as a keyboard 40 and a pointing device 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB) or a network interface card. A monitor 47 or other type of display device is also connected to the system bus 23 via an interface, such as a video adapter 48. In addition to the monitor, personal computers typically include other peripheral output devices, not shown, such as speakers and printers.

The personal computer 20 may operate in a networked environment using logical connections to one or more remote computers, such as a remote computer 49. The remote computer 49 may be another personal computer, a server, a router, a network PC, a peer device or other common network node, and typically includes many or all of the elements described above relative to the personal computer 20, although only a memory storage device 50 has been illustrated. The logical connections depicted include a local area network (LAN) 51 and a wide area network (WAN) 52. Such networking environments are commonplace in offices, enterprise-wide computer networks, intranets and, inter alia, the Internet.

When used in a LAN networking environment, the personal computer 20 is connected to local network 51 through network interface or adapter 53. When used in a WAN networking environment, the personal computer 20 typically includes modem 54 or other means for establishing communications over WAN 52. The modem 54, which may be internal or external, is connected to system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

It will be appreciated by persons skilled in the art that numerous variations and/or modifications may be made to the invention as shown in the specific embodiments without departing from the scope of the invention as broadly described. For example, while the described embodiments relate to obtaining a dyskinesia score and a bradykinesia score for an idiopathic Parkinson's disease patient treated with L-Dopa, it is to be appreciated that either score may be obtained alone, and either or both scores may be obtained for a person experiencing kinesic symptoms from other causes.

With regard to the Bradykinesia Scoring Algorithm, in BK7 the value in each of the sub-bands A to H identified in BK6 were weighted and $MSP_{MAX}$ was identified from the weighted band values. The Bradykinesia Score was then calculated according to the equation BK=10 log 10(MSP-max×PKi) defined in BK10. In an optional embodiment, a single 0.8 Hz sub-band which contains the maximum mean spectral power $SP_{maxi}$ may be identified and may replace MSPmax.

In DK4 of the Dyskinesia Scoring Algorithm $Acc_i$ is used as a threshold below which data is deemed to represent "reduced movement". In this, or an optional embodiment, a minimum threshold for $Acc_i$ could be set at for example an arbitrary low level or generated in response to a very low BK score.

It is to be appreciated that the present invention could for example be applied to individual assessment of hyperkinetic movements such as dystonia, chorea and/or myoclonus. The dyskinesia assessed by alternative embodiments of the present invention could for example arise from Huntington's disease, cervical dystonia, restless legs syndrome, paroxysmal kinesigenic dyskinesia, sleep disorders of movement, tics (stereotyped movements that are normal but out of context), Tourettes syndrome, tardive dyskinesia, tardive Tourettes, Halaroidan, Acanthocytosis, Hallervorden-Spatz or Pantothene Kinase deficiency, or Sagawa syndrome.

The bradykinesia or hypokinetic movement assessed by alternative embodiments of the present invention could arise from Multi Systems Atrophy, Striatonigral degeneration, progressive Supranuclear palsy, Olivopontocerebellar degeneration, Corticobasal ganglionic degeneration, Huntington's disease, drug induced Parkinsonism, trauma induced Parkinsonism, Pallido Luysian degeneration or Vascular Parkinsonism.

Another embodiment of the invention comprises an accelerometer (ADXL330) which is sampled by a Philips ARM-Based Microcontroller LPC2138 and data is stored onboard the device in an SD-Flash Memory card for later manual download to PC for analysis. The device is programmed to record from the patient for 16 hours per day for 4 days without recharge because the patients have difficulty with conventional charging. Data is date and time stamped and includes a header with patient details. The service provider is able to program the patient details, time of start and end for each day, and the number of days to record; all to be stored in datafile header.

The device records acceleration in three axes; X, Y, Z using a DC-10 Hz bandwidth (sampled @ 100 Hz per channel). The signal is calibrated in "gravity—g" and acceleration is measured from between +4 g and −4 g. A Real Time Clock is able to be programmed by the neurologist or service provider to start recording at some prescribed date and time in the future. Most likely the next day and first thing in the morning. The device records for a default time span of 6:00 am to 10:00 pm each day, but this time span is programmable by the neurologist or service provider. The number of days of recording defaults to 3 full days, but can be programmed in the range of 1 to 7 days or more. This device further provides for an input to be captured of a date and time that medication was taken. This could be the patient communicating with the wrist device to signal that medication has been taken.

At night, when the patient is in bed and the data logger is removed from the wrist, the datalogger will be placed in a cradle for battery charging and downloading of data to the central server or the doctor's own server.

The present embodiments are, therefore, to be considered in all respects as illustrative and not restrictive.

The invention claimed is:

1. An automated method of determining a bradykinetic state of a person, which is a state characterized by slowness of movement relative to a normally kinetic person and in which movements involving peaks of acceleration have strong low frequency components, the method comprising:
obtaining a time series of accelerometer data in real-time from an accelerometer worn on an extremity of the person, the time series of accelerometer data being representative of movement of the person over an extended period of time, wherein the time series of accelerometer data is obtained while the accelerometer is oriented to be sensitive to at least one of pronation and supination movements of the person and is attached to at least a limb of the person;
filtering, by a band pass filter, the accelerometer data to extract filtered data for a band of interest, wherein the band of interest has a lower end cut off frequency selected to remove DC;
extracting, by a computer processor, a plurality of bins of acceleration data from the time series of the filtered accelerometer data;

searching, by the computer processor, the data in each of the plurality of bins to identify a time window of peak acceleration, the time window within a given bin comprising at least two data samples that capture accelerometer data for a single movement having a peak acceleration relative to other movements observed within the plurality of bins; and processing, by the computer processor, data in the time windows of peak acceleration to determine:

spectral components for each of the single movements having peak acceleration; and an objective measure of the extent to which the single movements having peak acceleration identified within the plurality of bins of acceleration data are slower than expected from a normally kinetic person and indicative of bradykinesia based upon a comparative statistical analysis of the determined sets of spectral components of the single movements of peak acceleration that occur over the extended period of time.

2. The method according to claim 1, wherein the plurality of bins of acceleration data are of a time duration selected to be small enough that relatively regular measures of the extent to which the single movements having peak acceleration are slower than expected from a normally kinetic person and indicative of bradykinesia are determinable, while being long enough to provide a reasonable likelihood of a significant movement by the person during that bin.

3. The method according to claim 2, wherein the plurality of bins have durations within the range of 15 seconds to four minutes.

4. The method according to claim 1, wherein the searching comprises using a moving mean having a window length in a range of 0.02 seconds to 30 seconds in order to find a maxima.

5. The method according to claim 1, further comprising obtaining a sub-bin which comprises a plurality of data points both before and after a peak acceleration $PK_i$, and wherein the plurality of data points is a number of data points which is a power of two, and wherein the sub-bin is symmetrically positioned about the peak acceleration, and wherein the data points cover a period of time in a range of 0.5 seconds to 30 seconds.

6. The method according to claim 5, further comprising performing a spectral analysis of the sub-bin to obtain sub-band spectral measures, and wherein the sub-band spectral measures are of a width in the range of 0.6 Hz to 1 Hz.

7. The method according to claim 6, further comprising applying a weighting to at least a subset of the sub-band spectral measures to produce a weighted mean spectral power ($MSP_i$), wherein a greater measure of the extent to which the single movements having peak acceleration are slower than expected from a normally kinetic person and indicative of bradykinesia is given when the maximum ($MSP_i$) is small and exists in lower frequency sub-bands, and a lesser measure is given when the maximum ($MSP_i$) is high and exists in higher frequency sub-bands.

8. The method according to claim 7, further comprising:

selecting a plurality n of consecutive bins;

determining a peak acceleration ($PK_i$) and a $MSP_i$ for each selected bin, and from across the n bins selecting the largest value of $PK_i$ ($PK_{i,max}$); and computing at least one bradykinesia score BK according to at least one of the following formulae:

$$BK = PK_{i,max} \times MSP_{i,max};$$

and $$BK = A \times \log_c (PK_{i,max} \times MSP_{i,max}) - B$$

where A, c and B are selectable tuning constants and $MSP_{i,max}$ is the largest value of $MSP_i$.

9. The method according to claim 8, further comprising calculating a cumulative measure comprising a sum of individual measures determined in order to provide a cumulative indication of the bradykinetic state.

10. The method of claim 4 wherein the window length is a fraction of the duration of a human motion.

11. The method according to claim 8, wherein a moving median or moving average of the at least one measure of the extent to which the single movements having peak acceleration are slower than expected from a normally kinetic person and indicative of bradykinesia within a moving window is calculated, to give a probabilistic determination of the likelihood of bradykinetic behaviour.

12. The method according to claim 5, further comprising performing a spectral analysis of the sub-bin to obtain sub-band spectral measures, and wherein the sub-band spectral measures are of a width in the range of 0.1 Hz to 2 Hz.

13. The method of claim 1, further comprising:

displaying, on a visual monitor, an involuntary movement score corresponding to the objective measure determined in the processing step.

14. The method of claim 1, wherein the filtering causes a reduction of accelerometer data.

15. The method of claim 1, wherein the limb is an arm of the person and the accelerometer is worn on a distally located part thereof.

16. A wearable device to assist in determining a bradykinetic state of a person, which is a state characterized by slowness of movement relative to a normally kinetic person and in which movements involving peaks of acceleration have strong low frequency components, the device comprising:

an accelerometer arranged to be worn on at least a limb of the person, wherein the accelerometer is oriented to be sensitive to at least one of pronation and supination movements of the person;

a band pass filter for band pass filtering a time series of accelerometer data obtained in real-time from the accelerometer worn on at least the limb of the person to extract filtered data for a band of interest, the time series of accelerometer data being representative of movement of the person over an extended period of time, wherein the band of interest has a lower end cut off frequency selected to remove DC; and a processor configured to perform operations comprising:

extracting a plurality of bins of filtered accelerometer data from the time series of the accelerometer data, searching the data in each of the plurality of bins to identify a time window of peak acceleration, the time window within a given bin comprising at least two data samples that capture filtered accelerometer data for a single movement having a peak acceleration relative to other movements observed within the given bin, and processing the data in the time windows of peak acceleration to determine:

spectral components for each of the single movements having peak acceleration; and an objective measure of the extent to which the single movements having peak acceleration identified within the plurality of bins of filtered accelerometer data are slower than expected from a normally kinetic person and indicative of bradykinesia based upon a comparative statistical analysis of the determined sets of spectral components of the single movements of peak acceleration that occur over the extended period of time.

17. A non-transitory computer program product for determining a bradykinetic state of a person, which is a state characterized by slowness of movement relative to a normally kinetic person and in which movements involving peaks of acceleration have strong low frequency components, the computer program product comprising:
a processor;
a memory containing a computer-executable instruction that configures the processor to:
 obtain a time series of data in real-time from an accelerometer worn on an extremity of the person, the time series of accelerometer data being representative of movement of the person over an extended period of time, wherein the time series of accelerometer data is obtained while the accelerometer is oriented to be sensitive to at least one of pronation and supination movements of the person and is attached to at least a limb of the person;
 band pass filter accelerometer data to extract filtered data for a band of interest, wherein the band of interest has a lower end cut off frequency selected to remove DC;
 extract a plurality of bins of acceleration data from the time series of the filtered accelerometer data;
 search the data in each of the plurality of bins to identify a time window of peak acceleration, the time window within a given bin comprising at least two samples that capture accelerometer data for a single movement having a peak acceleration relative to other movements observed within the given bin; and
 process the data in the time windows of peak acceleration to determine:
  spectral components for each of the single movements having peak acceleration; and
  an objective measure of the extent to which the single movements having peak acceleration identified within the plurality of bins of acceleration data are slower than expected from a normally kinetic person and indicative of bradykinesia based upon a comparative statistical analysis of the determined sets of spectral components of the single movements of peak acceleration that occur over the extended period of time.

* * * * *

UNITED STATES PATENT AND TRADEMARK OFFICE
CERTIFICATE OF CORRECTION

PATENT NO. : 9,826,921 B2
APPLICATION NO. : 12/997540
DATED : November 28, 2017
INVENTOR(S) : Robert Irwin Griffiths et al.

Page 1 of 1

It is certified that error appears in the above-identified patent and that said Letters Patent is hereby corrected as shown below:

On the Title Page

Column 1, (86) PCT No., Line 1:
Please delete "PCT/SU2009/000751" and insert --PCT/AU2009/000751--

Signed and Sealed this
Nineteenth Day of June, 2018

Andrei Iancu
*Director of the United States Patent and Trademark Office*